United States Patent
Kim et al.

(10) Patent No.: US 7,674,617 B2
(45) Date of Patent: Mar. 9, 2010

(54) MIRNA MOLECULES ISOLATED FROM HUMAN EMBRYONIC STEM CELL

(75) Inventors: Kye-Seong Kim, Seoul (KR); Mi-Ra Suh, Seoul (KR); Vit-Narry Kim, Seoul (KR)

(73) Assignee: College of Medicine, Pochon Cha University -Academic Cooperation Foundation, Kyunggi-Do (KR)

( * ) Notice: Subject to any disclaimer, the term of this patent is extended or adjusted under 35 U.S.C. 154(b) by 588 days.

(21) Appl. No.: 10/582,915

(22) PCT Filed: Dec. 15, 2004

(86) PCT No.: PCT/KR2004/003308

§ 371 (c)(1),
(2), (4) Date: Jun. 14, 2006

(87) PCT Pub. No.: WO2005/056797

PCT Pub. Date: Jun. 23, 2005

(65) Prior Publication Data

US 2008/0050722 A1    Feb. 28, 2008

Related U.S. Application Data

(60) Provisional application No. 60/529,098, filed on Dec. 15, 2003.

(51) Int. Cl.
| C12N 15/00 | (2006.01) |
| C12Q 1/68 | (2006.01) |
| C07H 21/04 | (2006.01) |
| A61K 31/70 | (2006.01) |

(52) U.S. Cl. ................ 435/320.1; 536/24.3; 536/24.31; 536/24.33; 435/6; 514/44

(58) Field of Classification Search ....................... None
See application file for complete search history.

(56) References Cited

FOREIGN PATENT DOCUMENTS

WO    WO 03/029459 A2    4/2003

OTHER PUBLICATIONS

Houbaviy et al. Developmental Cell, vol. 5, 351-358, Aug. 2003.*
Houbaviy et al., "Embryonic Stem Cell-Specific MicroRNAs," *Developmental Cell*, 2003, vol. 5, pp. 351-358, Cell Press, Cambridge, MA, U.S.A.
Lagos-Quintana et al., "New microRNAs from mouse and human," *RNA*, 2003, vol. 9, No. 2, pp. 175-179, Cold Spring Harbor Laboratory Press, New York, New York.
Carrington et al., "Role of MicroRNAs in Plant and Animal Development," *Science*, 2003, vol. 301, No. 5631, pp. 336-338, American Association for the Advancement of Science, Washington, D.C.

* cited by examiner

*Primary Examiner*—Janet L. Epps-Smith
(74) *Attorney, Agent, or Firm*—Buchanan Ingersoll & Rooney PC

(57) ABSTRACT

The present invention relates to novel miRNA molecules, more particularly to novel miRNA molecules isolated from human embryonic stem cells. The miRNA molecules provided by the present invention can be usefully used as a molecular marker for early developmental stages of undifferentiated human embryonic stem cells. Also, the miRNA molecules of the present invention may play an important role in the regulation of mammalian embryonic stem cells. Therefore, the miRNA molecules can be usefully used for analyzing regulatory networks of human embryonic stem cells.

12 Claims, 6 Drawing Sheets

FIG. 3

A miR-302b*~302b~302c*~302c~302a*~302a~302d~367 (chromosome 4)

```
Template                   5'                                                                              3' miR-302b* and 302b         CA ACTTTAACACATGGAAGTGCTTTCT GTG---ACTTTAAAAGTAAGTGCTTCCATGTTTTAGTAGGA-
miR-302c* and 302c         --GCTTTAACATGGGGGGTACCTGCTG TG--TGAAACAAAAGTAAGTGCTTCCATGTTTCAGTGGAGG
miR-302a* and 302a         ---CTTAAACGTGGATGGTACTTGCTT GAAACTAAAGAAGTAAGTGCTTCCATGTTTTGGTGATGG
miR-302d                   -- ACTTTAACATGGAGGCACTTGCTGTGACATGACAAAAATAAGTGCTTCCATGTTTGAGTGTGG-
                               ***  ***       *** *      *   *   *    ***************
concensus                    TAAGTGCTTCCATGTTTNNGTNN
```

B miR-371~372~373*~373 (chromosome 19)

```
Template                   5'                                                              3' miR-371                    TGTGGCACTCAAACTGTGGGGCACTTTCTGCTCTCTG-GT--GAAAGTGCCGCCATCTTTTGAGTGTTA
miR-372                    TGTGGGCCTCAAA-TGTGAGCACTATTCTGATGTCCA-AGTGGAAAGTGCTGCGA-CATTGAGCGTCA
miR-373* and 373           -GGGATACTTCAAAATGGGGGCGCTTTCC TTTTGTCTGTACTGGGAAGTGCTTCGA-TTTGGGGTGCC
                              ****  ****   **   *  *   *  *              **   **   ****
concensus                      GTGCNNCNA-NNTTNGNGNGT
```

FIG. 5
a) miR-302b*~302b~302c*~302c~302a*~302a~302d~367 (chromosome 4)
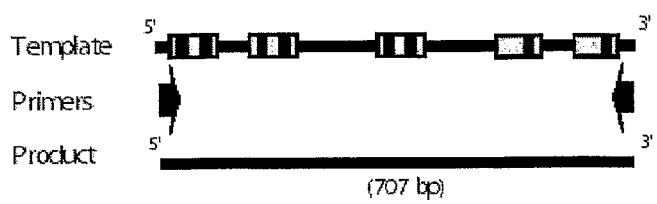
b) miR-371~372~373*~373 (chromosome 19)
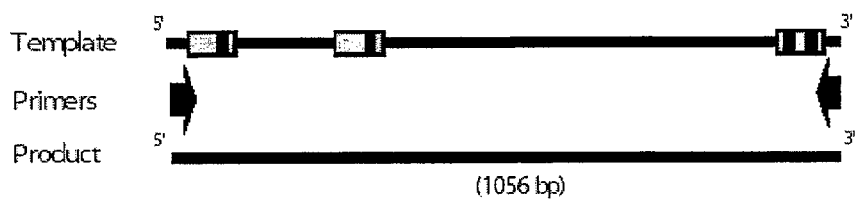
c) let-7a-1
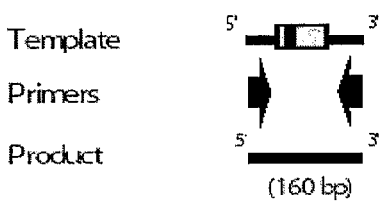
d) miR-30a~30a*
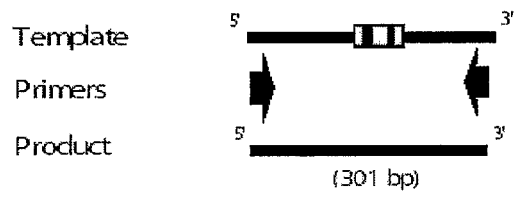

A: miR-302b*~302b~302c*~302c~302a*~302a~302d~367
B: miR-371~372~373*~373
C: human β-actin

SEQUENCE LISTING

<160> NUMBER OF SEQ ID NOS: 99

<210> SEQ ID NO 1
<211> LENGTH: 23
<212> TYPE: RNA
<213> ORGANISM: Homo sapiens

<400> SEQUENCE: 1
acuuuaacau ggaagugcuu ucu                          23

<210> SEQ ID NO 2
<211> LENGTH: 23
<212> TYPE: RNA
<213> ORGANISM: Homo sapiens

<400> SEQUENCE: 2
uaagugcuuc cauguuuuag uag                          23

<210> SEQ ID NO 3
<211> LENGTH: 22
<212> TYPE: RNA
<213> ORGANISM: Homo sapiens

<400> SEQUENCE: 3
uuuaacaugg ggguaccugc ug                           22

<210> SEQ ID NO 4
<211> LENGTH: 23
<212> TYPE: RNA
<213> ORGANISM: Homo sapiens

<400> SEQUENCE: 4
uaagugcuuc cauguuucag ugg                          23

<210> SEQ ID NO 5
<211> LENGTH: 22
<212> TYPE: RNA
<213> ORGANISM: Homo sapiens

<400> SEQUENCE: 5
uaaacgugga uguacuugcu uu                           22

<210> SEQ ID NO 6
<211> LENGTH: 23
<212> TYPE: RNA
<213> ORGANISM: Homo sapiens

<400> SEQUENCE: 6
uaagugcuuc cauguuugag ugu                          23

<210> SEQ ID NO 7
<211> LENGTH: 22
<212> TYPE: RNA
<213> ORGANISM: Homo sapiens

<400> SEQUENCE: 7
aauugcacuu uagcaauggu ga                           22

<210> SEQ ID NO 8
<211> LENGTH: 23
<212> TYPE: RNA
<213> ORGANISM: Homo sapiens

<400> SEQUENCE: 8
uaauacugcc ggguaaugau gga                                           23

<210> SEQ ID NO 9
<211> LENGTH: 22
<212> TYPE: RNA
<213> ORGANISM: Homo sapiens

<400> SEQUENCE: 9
acauagagga aauuccacgu uu                                            22

<210> SEQ ID NO 10
<211> LENGTH: 22
<212> TYPE: RNA
<213> ORGANISM: Homo sapiens

<400> SEQUENCE: 10
aaucauacac gguugaccua uu                                            22

<210> SEQ ID NO 11
<211> LENGTH: 21
<212> TYPE: RNA
<213> ORGANISM: Homo sapiens

<400> SEQUENCE: 11
aauaauacau gguugaucuu u                                             21

<210> SEQ ID NO 12
<211> LENGTH: 21
<212> TYPE: RNA
<213> ORGANISM: Homo sapiens

<400> SEQUENCE: 12
gccugcuggg guggaaccug g                                             21

<210> SEQ ID NO 13
<211> LENGTH: 21
<212> TYPE: RNA
<213> ORGANISM: Homo sapiens

<400> SEQUENCE: 13
gugccgccau cuuuugagug u                                             21

<210> SEQ ID NO 14
<211> LENGTH: 23
<212> TYPE: RNA
<213> ORGANISM: Homo sapiens

<400> SEQUENCE: 14
aaagugcugc gacauuugag cgu                                           23

<210> SEQ ID NO 15
<211> LENGTH: 22
<212> TYPE: RNA
<213> ORGANISM: Homo sapiens

<400> SEQUENCE: 15
acucaaaaug ggggcgcuuu cc                                            22

<210> SEQ ID NO 16
<211> LENGTH: 23
<212> TYPE: RNA

```
<213> ORGANISM: Homo sapiens

<400> SEQUENCE: 16
gaagugcuuc gauuugggg ugu                                         23

<210> SEQ ID NO 17
<211> LENGTH: 22
<212> TYPE: RNA
<213> ORGANISM: Homo sapiens

<400> SEQUENCE: 17
uuauaauaca accugauaag ug                                         22

<210> SEQ ID NO 18
<211> LENGTH: 23
<212> TYPE: RNA
<213> ORGANISM: Homo sapiens

<400> SEQUENCE: 18
uaagugcuuc cauguuugg uga                                         23

<210> SEQ ID NO 19
<211> LENGTH: 23
<212> TYPE: RNA
<213> ORGANISM: Homo sapiens

<400> SEQUENCE: 19
cagugcaaua guauugucaa agc                                        23

<210> SEQ ID NO 20
<211> LENGTH: 21
<212> TYPE: RNA
<213> ORGANISM: Homo sapiens

<400> SEQUENCE: 20
agggcccccc cucaauccug u                                          21

<210> SEQ ID NO 21
<211> LENGTH: 22
<212> TYPE: RNA
<213> ORGANISM: Homo sapiens

<400> SEQUENCE: 21
ugagguagua gguuguauag uu                                         22

<210> SEQ ID NO 22
<211> LENGTH: 22
<212> TYPE: RNA
<213> ORGANISM: Homo sapiens

<400> SEQUENCE: 22
uagcagcacg uaaauauugg cg                                         22

<210> SEQ ID NO 23
<211> LENGTH: 24
<212> TYPE: RNA
<213> ORGANISM: Homo sapiens

<400> SEQUENCE: 23
caaagugcuu acagugcagg uagu                                       24

<210> SEQ ID NO 24
<211> LENGTH: 23
```

```
<212> TYPE: RNA
<213> ORGANISM: Homo sapiens

<400> SEQUENCE: 24
ugugcaaauc caugcaaaac uga                                          23

<210> SEQ ID NO 25
<211> LENGTH: 23
<212> TYPE: RNA
<213> ORGANISM: Homo sapiens

<400> SEQUENCE: 25
uagcuuauca gacugauguu gac                                          23

<210> SEQ ID NO 26
<211> LENGTH: 22
<212> TYPE: RNA
<213> ORGANISM: Homo sapiens

<400> SEQUENCE: 26
uucaaguaau ccaggauagg cu                                           22

<210> SEQ ID NO 27
<211> LENGTH: 22
<212> TYPE: RNA
<213> ORGANISM: Homo sapiens

<400> SEQUENCE: 27
cuagcaccau cugaaaucgg uu                                           22

<210> SEQ ID NO 28
<211> LENGTH: 21
<212> TYPE: RNA
<213> ORGANISM: Homo sapiens

<400> SEQUENCE: 28
uagcaccauu ugaaaucagu g                                            21

<210> SEQ ID NO 29
<211> LENGTH: 21
<212> TYPE: RNA
<213> ORGANISM: Homo sapiens

<400> SEQUENCE: 29
uauugcacuu gucccggccu g                                            21

<210> SEQ ID NO 30
<211> LENGTH: 22
<212> TYPE: RNA
<213> ORGANISM: Homo sapiens

<400> SEQUENCE: 30
agcagcauug uacagggcua ug                                           22

<210> SEQ ID NO 31
<211> LENGTH: 22
<212> TYPE: RNA
<213> ORGANISM: Homo sapiens

<400> SEQUENCE: 31
uuaaggcacg cggugaaugc ca                                           22

<210> SEQ ID NO 32
```

```
<211> LENGTH: 22
<212> TYPE: RNA
<213> ORGANISM: Homo sapiens

<400> SEQUENCE: 32
cagugcaaug uuaaaagggc au                                                22

<210> SEQ ID NO 33
<211> LENGTH: 22
<212> TYPE: RNA
<213> ORGANISM: Homo sapiens

<400> SEQUENCE: 33
ugugacuggu ugaccagagg gg                                                22

<210> SEQ ID NO 34
<211> LENGTH: 23
<212> TYPE: RNA
<213> ORGANISM: Homo sapiens

<400> SEQUENCE: 34
uauggcuuuu uauuccuaug uga                                               23

<210> SEQ ID NO 35
<211> LENGTH: 23
<212> TYPE: RNA
<213> ORGANISM: Homo sapiens

<400> SEQUENCE: 35
acuccauuug uuuugaugau gga                                               23

<210> SEQ ID NO 36
<211> LENGTH: 24
<212> TYPE: RNA
<213> ORGANISM: Homo sapiens

<400> SEQUENCE: 36
agcuacaucu ggcuacuggg ucuc                                              24

<210> SEQ ID NO 37
<211> LENGTH: 23
<212> TYPE: DNA
<213> ORGANISM: Artificial Sequence
<220> FEATURE:
<223> OTHER INFORMATION: probe for miR-302b*

<400> SEQUENCE: 37
agaaagcact tccatgttaa agt                                               23

<210> SEQ ID NO 38
<211> LENGTH: 23
<212> TYPE: DNA
<213> ORGANISM: Artificial Sequence
<220> FEATURE:
<223> OTHER INFORMATION: probe for miR-302b

<400> SEQUENCE: 38
ctactaaaac atggaagcac tta                                               23

<210> SEQ ID NO 39
<211> LENGTH: 22
<212> TYPE: DNA
<213> ORGANISM: Artificial Sequence
<220> FEATURE:
<223> OTHER INFORMATION: probe for miR-302c*
```

<400> SEQUENCE: 39
cagcaggtac ccccatgtta aa                                              22

<210> SEQ ID NO 40
<211> LENGTH: 23
<212> TYPE: DNA
<213> ORGANISM: Artificial Sequence
<220> FEATURE:
<223> OTHER INFORMATION: probe for miR-302c

<400> SEQUENCE: 40
ccactgaaac atggaagcac tta                                             23

<210> SEQ ID NO 41
<211> LENGTH: 22
<212> TYPE: DNA
<213> ORGANISM: Artificial Sequence
<220> FEATURE:
<223> OTHER INFORMATION: probe for miR-302a*

<400> SEQUENCE: 41
aaagcaagta ctaccacgtt ta                                              22

<210> SEQ ID NO 42
<211> LENGTH: 23
<212> TYPE: DNA
<213> ORGANISM: Artificial Sequence
<220> FEATURE:
<223> OTHER INFORMATION: probe for miR-302a

<400> SEQUENCE: 42
tcaccaaaac atggaagcac tta                                             23

<210> SEQ ID NO 43
<211> LENGTH: 23
<212> TYPE: DNA
<213> ORGANISM: Artificial Sequence
<220> FEATURE:
<223> OTHER INFORMATION: probe for miR-302d

<400> SEQUENCE: 43
acactcaaac atggaagcac tta                                             23

<210> SEQ ID NO 44
<211> LENGTH: 22
<212> TYPE: DNA
<213> ORGANISM: Artificial Sequence
<220> FEATURE:
<223> OTHER INFORMATION: probe for miR-367

<400> SEQUENCE: 44
tcaccattgc taaagtgcaa tt                                              22

<210> SEQ ID NO 45
<211> LENGTH: 23
<212> TYPE: DNA
<213> ORGANISM: Artificial Sequence
<220> FEATURE:
<223> OTHER INFORMATION: probe for miR-200c

<400> SEQUENCE: 45
tccatcatta cccggcagta tta                                             23

<210> SEQ ID NO 46

```
<211> LENGTH: 22
<212> TYPE: DNA
<213> ORGANISM: Artificial Sequence
<220> FEATURE:
<223> OTHER INFORMATION: probe for miR-368

<400> SEQUENCE: 46
aaacgtggaa tttcctctat gt                                          22

<210> SEQ ID NO 47
<211> LENGTH: 22
<212> TYPE: DNA
<213> ORGANISM: Artificial Sequence
<220> FEATURE:
<223> OTHER INFORMATION: probe for miR-154*

<400> SEQUENCE: 47
aataggtcaa ccgtgtatga tt                                          22

<210> SEQ ID NO 48
<211> LENGTH: 21
<212> TYPE: DNA
<213> ORGANISM: Artificial Sequence
<220> FEATURE:
<223> OTHER INFORMATION: probe for miR-369

<400> SEQUENCE: 48
aaagatcaac catgtattat t                                           21

<210> SEQ ID NO 49
<211> LENGTH: 21
<212> TYPE: DNA
<213> ORGANISM: Artificial Sequence
<220> FEATURE:
<223> OTHER INFORMATION: probe for miR-370

<400> SEQUENCE: 49
ccaggttcca ccccagcagg c                                           21

<210> SEQ ID NO 50
<211> LENGTH: 23
<212> TYPE: DNA
<213> ORGANISM: Artificial Sequence
<220> FEATURE:
<223> OTHER INFORMATION: probe for miR-301

<400> SEQUENCE: 50
gctttgacaa tactattgca ctg                                         23

<210> SEQ ID NO 51
<211> LENGTH: 21
<212> TYPE: DNA
<213> ORGANISM: Artificial Sequence
<220> FEATURE:
<223> OTHER INFORMATION: probe for miR-371

<400> SEQUENCE: 51
acactcaaaa gatggcggca c                                           21

<210> SEQ ID NO 52
<211> LENGTH: 23
<212> TYPE: DNA
<213> ORGANISM: Artificial Sequence
<220> FEATURE:
<223> OTHER INFORMATION: probe for miR-372

<400> SEQUENCE: 52
```
acgctcaaat gtcgcagcac ttt                                                    23

<210> SEQ ID NO 53
<211> LENGTH: 23
<212> TYPE: DNA
<213> ORGANISM: Artificial Sequence
<220> FEATURE:
<223> OTHER INFORMATION: probe for miR-373

<400> SEQUENCE: 53
acaccccaaa atcgaagcac ttc                                                    23

<210> SEQ ID NO 54
<211> LENGTH: 22
<212> TYPE: DNA
<213> ORGANISM: Artificial Sequence
<220> FEATURE:
<223> OTHER INFORMATION: probe for miR-373*

<400> SEQUENCE: 54
ggaaagcgcc cccattttga gt                                                     22

<210> SEQ ID NO 55
<211> LENGTH: 21
<212> TYPE: DNA
<213> ORGANISM: Artificial Sequence
<220> FEATURE:
<223> OTHER INFORMATION: probe for miR-296

<400> SEQUENCE: 55
acaggattga gggggggccc t                                                      21

<210> SEQ ID NO 56
<211> LENGTH: 22
<212> TYPE: DNA
<213> ORGANISM: Artificial Sequence
<220> FEATURE:
<223> OTHER INFORMATION: probe for miR-374

<400> SEQUENCE: 56
cacttatcag gttgtattat aa                                                     22

<210> SEQ ID NO 57
<211> LENGTH: 22
<212> TYPE: DNA
<213> ORGANISM: Artificial Sequence
<220> FEATURE:
<223> OTHER INFORMATION: probe for let-7a-1

<400> SEQUENCE: 57
aactatacaa cctactacct ca                                                     22

<210> SEQ ID NO 58
<211> LENGTH: 22
<212> TYPE: DNA
<213> ORGANISM: Artificial Sequence
<220> FEATURE:
<223> OTHER INFORMATION: probe for miR-16

<400> SEQUENCE: 58
cgccaatatt tacgtgctgc ta                                                     22

<210> SEQ ID NO 59
<211> LENGTH: 24
<212> TYPE: DNA

```
<213> ORGANISM: Artificial Sequence
<220> FEATURE:
<223> OTHER INFORMATION: probe for miR-17-5p

<400> SEQUENCE: 59
actacctgca ctgtaagcac tttg                                          24

<210> SEQ ID NO 60
<211> LENGTH: 23
<212> TYPE: DNA
<213> ORGANISM: Artificial Sequence
<220> FEATURE:
<223> OTHER INFORMATION: probe for miR-19b

<400> SEQUENCE: 60
tcagttttgc atggatttgc aca                                           23

<210> SEQ ID NO 61
<211> LENGTH: 23
<212> TYPE: DNA
<213> ORGANISM: Artificial Sequence
<220> FEATURE:
<223> OTHER INFORMATION: probe for miR-21

<400> SEQUENCE: 61
gtcaacatca gtctgataag cta                                           23

<210> SEQ ID NO 62
<211> LENGTH: 22
<212> TYPE: DNA
<213> ORGANISM: Artificial Sequence
<220> FEATURE:
<223> OTHER INFORMATION: probe for miR-26a

<400> SEQUENCE: 62
agcctatcct ggattacttg aa                                            22

<210> SEQ ID NO 63
<211> LENGTH: 22
<212> TYPE: DNA
<213> ORGANISM: Artificial Sequence
<220> FEATURE:
<223> OTHER INFORMATION: probe for miR-29

<400> SEQUENCE: 63
aaccgattcc agatggagct ag                                            22

<210> SEQ ID NO 64
<211> LENGTH: 21
<212> TYPE: DNA
<213> ORGANISM: Artificial Sequence
<220> FEATURE:
<223> OTHER INFORMATION: probe for miR-29b-2

<400> SEQUENCE: 64
cactgatttc aaatggtgct a                                             21

<210> SEQ ID NO 65
<211> LENGTH: 21
<212> TYPE: DNA
<213> ORGANISM: Artificial Sequence
<220> FEATURE:
<223> OTHER INFORMATION: probe for miR-92

<400> SEQUENCE: 65
caggccggga caagtgcaat a                                             21
```

<210> SEQ ID NO 66
<211> LENGTH: 22
<212> TYPE: DNA
<213> ORGANISM: Artificial Sequence
<220> FEATURE:
<223> OTHER INFORMATION: probe for miR-103

<400> SEQUENCE: 66
catagccctg tacaatgctg ct                                          22

<210> SEQ ID NO 67
<211> LENGTH: 22
<212> TYPE: DNA
<213> ORGANISM: Artificial Sequence
<220> FEATURE:
<223> OTHER INFORMATION: probe for miR-124a #

<400> SEQUENCE: 67
tggcattcac cgcgtgcctt aa                                          22

<210> SEQ ID NO 68
<211> LENGTH: 22
<212> TYPE: DNA
<213> ORGANISM: Artificial Sequence
<220> FEATURE:
<223> OTHER INFORMATION: probe for miR-130a #

<400> SEQUENCE: 68
atgccctttt aacattgcac tg                                          22

<210> SEQ ID NO 69
<211> LENGTH: 22
<212> TYPE: DNA
<213> ORGANISM: Artificial Sequence
<220> FEATURE:
<223> OTHER INFORMATION: probe for miR-134 #

<400> SEQUENCE: 69
cccctctggt caaccagtca ca                                          22

<210> SEQ ID NO 70
<211> LENGTH: 23
<212> TYPE: DNA
<213> ORGANISM: Artificial Sequence
<220> FEATURE:
<223> OTHER INFORMATION: probe for miR-135-2 #

<400> SEQUENCE: 70
tcacatagga ataaaaagcc ata                                         23

<210> SEQ ID NO 71
<211> LENGTH: 23
<212> TYPE: DNA
<213> ORGANISM: Artificial Sequence
<220> FEATURE:
<223> OTHER INFORMATION: probe for miR-136 #

<400> SEQUENCE: 71
tccatcatca aaacaaatgg agt                                         23

<210> SEQ ID NO 72
<211> LENGTH: 24
<212> TYPE: DNA
<213> ORGANISM: Artificial Sequence
<220> FEATURE:

-continued

<223> OTHER INFORMATION: probe for miR-222

<400> SEQUENCE: 72
gagacccagt agccagatgt agct                                      24

<210> SEQ ID NO 73
<211> LENGTH: 23
<212> TYPE: RNA
<213> ORGANISM: Homo Sapiens
<220> FEATURE:
<221> NAME/KEY: variation
<222> LOCATION: 18, 19, 22, 23
<223> OTHER INFORMATION: n=u or a or g or c

<400> SEQUENCE: 73
uaagugcuuc cauguuunng unn                                       23

<210> SEQ ID NO 74
<211> LENGTH: 20
<212> TYPE: DNA
<213> ORGANISM: Artificial Sequence
<220> FEATURE:
<223> OTHER INFORMATION: forward primer for miR-302b*~302b~302c*~302c~
      302a*~302a~302d~367 cluster

<400> SEQUENCE: 74
gggctcccTT caactttaac                                           20

<210> SEQ ID NO 75
<211> LENGTH: 30
<212> TYPE: DNA
<213> ORGANISM: Artificial Sequence
<220> FEATURE:
<223> OTHER INFORMATION: reverse primer for miR-302b*~302b~302c*~302c~
      302a*~302a~302d~367 cluster

<400> SEQUENCE: 75
attctgtcat tggcttaaca atccatcacc                                30

<210> SEQ ID NO 76
<211> LENGTH: 20
<212> TYPE: DNA
<213> ORGANISM: Artificial Sequence
<220> FEATURE:
<223> OTHER INFORMATION: forward primer for miR-371~372~373*~373 cluster

<400> SEQUENCE: 76
cgatcgccgc cttgccgcat                                           20

<210> SEQ ID NO 77
<211> LENGTH: 30
<212> TYPE: DNA
<213> ORGANISM: Artificial Sequence
<220> FEATURE:
<223> OTHER INFORMATION: reverse primer for miR-371~372~373*~373 cluster

<400> SEQUENCE: 77
tggttcgtga tgccctactc aaacagggac                                30

<210> SEQ ID NO 78
<211> LENGTH: 30
<212> TYPE: DNA
<213> ORGANISM: Artificial Sequence
<220> FEATURE:
<223> OTHER INFORMATION: forward primer for miR-30a~30a* cluster

<400> SEQUENCE: 78
attgctgttt gaatgaggct tcagtacttt    30

<210> SEQ ID NO 79
<211> LENGTH: 30
<212> TYPE: DNA
<213> ORGANISM: Artificial Sequence
<220> FEATURE:
<223> OTHER INFORMATION: reverse primer for miR-30a~30a* cluster

<400> SEQUENCE: 79
ttcagctttg taaaaatgta tcaaagagat    30

<210> SEQ ID NO 80
<211> LENGTH: 30
<212> TYPE: DNA
<213> ORGANISM: Artificial Sequence
<220> FEATURE:
<223> OTHER INFORMATION: forward primer for let-7a-1

<400> SEQUENCE: 80
gattcctttt caccattcac cctggatgtt    30

<210> SEQ ID NO 81
<211> LENGTH: 30
<212> TYPE: DNA
<213> ORGANISM: Artificial Sequence
<220> FEATURE:
<223> OTHER INFORMATION: reverse primer for let-7a-1

<400> SEQUENCE: 81
tttctatcag accgcctgga tgcagacttt    30

<210> SEQ ID NO 82
<211> LENGTH: 25
<212> TYPE: DNA
<213> ORGANISM: Artificial Sequence
<220> FEATURE:
<223> OTHER INFORMATION: forward primer for GAPDH

<400> SEQUENCE: 82
tgtcatcaat ggaaatccca tcacc    25

<210> SEQ ID NO 83
<211> LENGTH: 25
<212> TYPE: DNA
<213> ORGANISM: Artificial Sequence
<220> FEATURE:
<223> OTHER INFORMATION: reverse primer for GADPH

<400> SEQUENCE: 83
catgagtcct tccacgatac caaag    25

<210> SEQ ID NO 84
<211> LENGTH: 91
<212> TYPE: RNA
<213> ORGANISM: Artificial Sequence
<220> FEATURE:
<223> OTHER INFORMATION: miRNA precursor for miR-302b* and miR-302b

<400> SEQUENCE: 84 guugggugg cucccuucaa cuuuaacaug gaagugcuuu cugugacuuu aaaaguaagu    60
gcuuccaugu uuuaguagga gugaauccaa u    91

<210> SEQ ID NO 85

```
<211> LENGTH: 81
<212> TYPE: RNA
<213> ORGANISM: Artificial Sequence
<220> FEATURE:
<223> OTHER INFORMATION: miRNA precursor for miR-302c* and miR-302c

<400> SEQUENCE: 85 gggaucccu uugcuuuaac auggggguac cugcugugug aaacaaaagu aagugcuucc    60
auguuucagu ggaggugucu c                                            81

<210> SEQ ID NO 86
<211> LENGTH: 69
<212> TYPE: RNA
<213> ORGANISM: Artificial Sequence
<220> FEATURE:
<223> OTHER INFORMATION: miRNA precursor for miR-302a* and miR-302a

<400> SEQUENCE: 86
ccaccacuua aacguggaug uacuugcuuu gaaacuaaag aaguaagugc uuccauguuu    60
uggugaugg                                                          69

<210> SEQ ID NO 87
<211> LENGTH: 84
<212> TYPE: RNA
<213> ORGANISM: Artificial Sequence
<220> FEATURE:
<223> OTHER INFORMATION: miRNA precursor for miR-302d

<400> SEQUENCE: 87
aggggccccc ucuacuuuaa cauggaggca cuugcuguga caugacaaaa auaagugcuu    60
ccauguuuga gugggugguugu uccu                                       84

<210> SEQ ID NO 88
<211> LENGTH: 90
<212> TYPE: RNA
<213> ORGANISM: Artificial Sequence
<220> FEATURE:
<223> OTHER INFORMATION: miRNA precursor for miR-367

<400> SEQUENCE: 88
uggcuacagg ccauuacugu ugcuaauaug caacucuguu gaauauaaau uggaauugca    60
cuuuagcaau ggugauggau uguuaagcca                                    90

<210> SEQ ID NO 89
<211> LENGTH: 84
<212> TYPE: RNA
<213> ORGANISM: Artificial Sequence
<220> FEATURE:
<223> OTHER INFORMATION: miRNA precursor for miR-200c

<400> SEQUENCE: 89
ggcgggggcc cucgucuuac ccagcagugu uuggugcgg uugggagucu cuaauacugc    60
cggguaauga uggaggcccc uguc                                         84

<210> SEQ ID NO 90
<211> LENGTH: 86
<212> TYPE: RNA
<213> ORGANISM: Artificial Sequence
<220> FEATURE:
<223> OTHER INFORMATION: miRNA precursor for miR-368

<400> SEQUENCE: 90
uuugguauuu aaaaggugga uauuccuucu auguuuaugu uauuuauggu uaaacauaga    60
```

```
ggaaauucca cguuuucagu aucaaa                                          86

<210> SEQ ID NO 91
<211> LENGTH: 75
<212> TYPE: RNA
<213> ORGANISM: Artificial Sequence
<220> FEATURE:
<223> OTHER INFORMATION: miRNA precursor for miR-154*

<400> SEQUENCE: 91
uacuugaaga uagguauccg uguugccuuc gcuuuauuug ugacgaauca uacacgguug    60
accuauuuuu cagua                                                     75

<210> SEQ ID NO 92
<211> LENGTH: 69
<212> TYPE: RNA
<213> ORGANISM: Artificial Sequence
<220> FEATURE:
<223> OTHER INFORMATION: miRNA precursor for miR-369

<400> SEQUENCE: 92
uugaagggag augaccgugu uauauucgcu uuauugacuu cgaauaauac augguugauc    60
uuuucucag                                                            69

<210> SEQ ID NO 93
<211> LENGTH: 75
<212> TYPE: RNA
<213> ORGANISM: Artificial Sequence
<220> FEATURE:
<223> OTHER INFORMATION: miRNA precursor for miR-370

<400> SEQUENCE: 93
agacagagaa gccaggucac gucucugcag uuacacagcu cacgagugcc ugcuggggug    60
gaaccugguc ugucu                                                     75

<210> SEQ ID NO 94
<211> LENGTH: 84
<212> TYPE: RNA
<213> ORGANISM: Artificial Sequence
<220> FEATURE:
<223> OTHER INFORMATION: miRNA precursor for miR-301

<400> SEQUENCE: 94
cugcuaacga augcucugac uuuauugcac uacuguacuu uacagcuagc agugcaauag    60
uauugucaaa gcaucugaaa gcag                                           84

<210> SEQ ID NO 95
<211> LENGTH: 76
<212> TYPE: RNA
<213> ORGANISM: Artificial Sequence
<220> FEATURE:
<223> OTHER INFORMATION: miRNA precursor for miR-371

<400> SEQUENCE: 95
agccuguggc acucaaacug uggggggcacu uucugcucuc uggugaaagu gccgccaucu   60
uuugagucuu accgcu                                                    76

<210> SEQ ID NO 96
<211> LENGTH: 80
<212> TYPE: RNA
<213> ORGANISM: Artificial Sequence
<220> FEATURE:
```

```
<223> OTHER INFORMATION: miRNA precursor for miR-372

<400> SEQUENCE: 96
ucacccugug ggccucaaau guggagcacu auucugaugu ccaaguggaa agugcugcga    60
cauuugagcg ucaccgguga                                                80

<210> SEQ ID NO 97
<211> LENGTH: 75
<212> TYPE: RNA
<213> ORGANISM: Artificial Sequence
<220> FEATURE:
<223> OTHER INFORMATION: miRNA precursor for miR-373* and miR-373

<400> SEQUENCE: 97
acugggauac ucaaaauggg ggcgcuuucc uuuuugucug uacugggaag ugcuucgauu    60 uuggggmguguc ccugu                                                   75

<210> SEQ ID NO 98
<211> LENGTH: 72
<212> TYPE: RNA
<213> ORGANISM: Artificial Sequence
<220> FEATURE:
<223> OTHER INFORMATION: miRNA precursor for miR-296

<400> SEQUENCE: 98
cccuuccaga gggccccccc ucaauccugu ugugccuaau ucagaggguu ggguggaggc    60
ucuccugaag gg                                                        72

<210> SEQ ID NO 99
<211> LENGTH: 72
<212> TYPE: RNA
<213> ORGANISM: Artificial Sequence
<220> FEATURE:
<223> OTHER INFORMATION: miRNA precursor for miR-374

<400> SEQUENCE: 99
uacaucggcc auuauaauac aaccugauaa guguuauagc acuuaucaga uuguauugua    60
auugucugug ua                                                        72
```

MIRNA MOLECULES ISOLATED FROM HUMAN EMBRYONIC STEM CELL

FIELD OF THE INVENTION

The present invention relates to novel miRNA molecules, more specifically miRNA molecules isolated from human embryonic stem cell.

BACKGROUND OF THE INVENTION

Embryonic stem cells (ESCs) were first derived from mice and are now available from a variety of mammalian systems, including human. They are characterized by nearly unlimited self-renewal in an undifferentiated state under defined culture conditions while retaining differentiation capacity (Evans et. al., Nature, 292:154-156, 1981; Martin, Proc. Natl. Acad. Sci. U. S. A. 78: 7634-7638, 1981; Smith, Cold Spring Harbor Laboratory Press, New York, 2001). During differentiation in vitro, embryonic stem cells are able to develop into various kinds of specialized somatic cell types and recapitulate processes of early embryonic development. Thus, embryonic stem cells hold promise as an unlimited source for various clinical and biotechnological applications (Brustle, Science, 285:754-756, 1999; Martin, Proc. Natl. Acad. Sci. U. S. A. 78: 7634-7638, 1981; Li et al., Curr. Biol., 8:971-974, 1998; Pera et al., J. Cell. Sci., 113:5-10, 2000).

Currently a few molecular regulators are known to participate in the self-renewal and pluripotency of mouse embryonic stem (mES) cells. A POU family transcription factor Oct4, the classical marker of all pluripotent cells, is specifically expressed in pre-implantation embryos, epiblast, germ cells and pluripotent stem cell lines including embryonic stem cells, embryonic germ (EG) cells and embryonic carcinoma (EC) cells (Palmieri et al., Dev. Biol., 166:259-267, 1994; Yeom et al., Development, 122:881-894, 1996). Oct4 plays a critical role in the establishment and maintenance of pluripotent cells in a pluripotent state (Nichols et al., Cell, 95:379-391, 1998; Niwa et al., Nat. Genet., 24:372-376, 2000; Pesce et al., BioEssays, 20:722-732, 1998). Leukemia inhibitory factor (LIF) can maintain self-renewal of mouse embryonic stem cells through activation of Stat3. Oct4 and Stat3 each interact with various cofactors and regulate the expression of multiple target genes (Niwa et al., Gene Dev., 12:2048-2060, 1998). Two other transcription factors, Sox2 and FoxD3, have been shown to be essential for pluripotency in mice embryos (Avilion et al., Gene Dev., 17:126-140, 2003; Hanna et al., Gene Dev., 16:2650-2661, 2002). More recently, it was found that the homeoprotein Nanog is capable of maintaining self-renewal of mouse embryonic stem cell, independently of LIF/Stat3 (Chambers et al., Cell, 113:643-655, 2003; Mitsui et al., Cell, 113:631-642, 2003).

The first human embryonic stem cell line was established only recently (Thomson et al., Science, 282:1145-1147, 1998) and 12 lines are publicly available worldwide (NIH Human Embryonic Stem Cell Registry). Despite their great potential, human embryonic stem cells have not been a prolific source of information. This is mainly due to the technical difficulties in cell culture. Maintaining and expanding human embryonic stem cells require laborious and skill-intensive procedures. Moreover, the population-doubling time of human embryonic stem cells is almost three times longer than that of mouse embryonic stem cells (Amit et al., Dev. Biol., 227:27 1-278, 2000). There exist apparent differences in the characteristics of human embryonic stem cells compared to mouse embryonic stem cells in many aspects, including the regulation of self-renewal. Of the regulators found in mice, only a few including Oct4 play similar regulatory roles in human embryonic stem cells. Others such as LIF do not affect human embryonic stem cells in maintaining their self-renewal (Reubinoff et al., Nat. Biotechnol., 18:399-404, 2000). Dissecting the regulatory mechanism in human embryonic stem cells will greatly enhance the understanding of stem cells as well as their application.

Recent advances in small RNA research have implicated microRNAs (hereinafter, referred to as 'miRNAs') as important regulators of development and differentiation. miRNAs constitute a large family of non-coding small RNAs of ~22 nucleotides (nt) in length. Our understanding of miRNA function originates from studies of the developmentally regulated miRNAs lin-4 (Olsen and Ambros, Dev. Biol., 216:671-680, 1999; Lee et al., Cell, 75: 843-854, 1993; and Wightman et al., Cell, 75:855-862, 1993) and let-7 (Reinhart et al, Nature, 403:901-906, 2000) in Caenorhabditis elegans. By binding and inhibiting the translation of the target mRNA, the lin-4 and let-7 RNAs play an important role in regulating the timing of larval development. Another example is bantam RNA from Drosophila melanogaster, which is expressed in a temporal and tissue-specific manner during development, suppressing apoptosis and stimulating cell proliferation by inhibiting translation of hid mRNA (Brennecke et al., Cell, 113:25-26, 2003). Several mouse miRNAs including miR-181 were shown to modulate hematopoiesis (Chen et al., Science, 303:83-86, 2003). In plants, miRNAs show a high degree of complementarity to transcription factors that are significant in development (Aukerman and Sakai, Plant Cell, 2003; Chen, Science, 2003; Llave et al., Science, 297:2053-2056, 2002b; Palatnik et al., Nature, 425:257-263, 2003 and Rhoades et al., Cell, 110:513-520, 2002). These miRNAs induce target mRNA cleavage or translational repression, thereby facilitating plant development and organogenesis.

The expression of miRNAs is often regulated in tissue-specific and developmental stage-specific manners (Aravin et al., Dev. Cell, 5:337-350, 2003; Krichevsky et al., RNA, 9:1274-1281, 2003; Lagos-Quintana et al, Science, 294:853-858, 2002; Pasquinelli et al., Nature, 408-86-89, 2000 and Sempere et al., Dev. Biol. 259:9-18, 2003), although the regulatory mechanism is still largely unknown. The present inventors have previously shown that miRNAs are transcribed as long primary transcripts (termed pri-miRNAs) (Lee et al., EMBO J., 21:4663-4670, 2002). These primary transcripts are first trimmed into approximately 70 nt stem-loop forms (called pre-miRNAs) by the RNase III type protein, Drosha, in the nucleus (Lee et al., Nature, 425:415-419, 2003). Following this initial processing, pre-miRNAs get exported to the cytoplasm by Exportin-5 (Lund et al., Science, 303:95-98, 2003 and Yi et al., Genes Dev., 2003) and are subject to a second processing to generate the final product of approximately 22 nt mature miRNAs, by another RNase III type protein Dicer (Grishok et al., Cell, 106:23-24, 2001; Hutvagner et al., Science, 293:834-838, 2001; Ketting et al., Genes Dev., 15:2654-2659, 2001; and Knight and Bass, Science, 293:2269-2271, 2001). This stepwise processing and compartmentalization may allow for the fine regulation of miRNA biogenesis at multiple steps.

More than 300 miRNAs have been reported in diverse eukaryotic organisms so far (Aravin et al., Dev. Cell, 5:337-350, 2003; Dostie et al, RNA, 9:180-186, 2003; Grad et al., Mol. Cell., 11:1253-1263, 2003; Lagos-Quintana et al., Science, 294:853-858, 2001; Lagos-Quintana et al., Curr Biol. 12:735-739, 2002; Lagos-Quintana et al., RNA, 9:175-179, 2003; Lai et al., Genome Biol., 4, R42, 2003; Lau et al., Science, 294:858-862, 2001; Lee and Ambros, Science, 294: 862-864, 2001; Lee et al., Cell, 75:843-854, 1993; Lim et al., Genes Dev., 2, 2, 2003b; Llave et al., *Plant Cell,* 14:1605-1619, 2002a; Mourelatos et al., *Genes Dev.,* 16:720-728, 2002; Park et al., *Curr. Biol.,* 12:1484-1495, 2002; Reinhart et al., *Nature,* 403-901-906, 2000 and Reinhart et al., *Genes Dev.,* 16:1616-1626, 2002). The majority of miRNA genes were discovered through cDNA cloning from size-fractionated RNA samples. Recently, additional miRNA genes have been identified using computational procedures from the vertebrates, *C. elegans* and *Drosophila*. A bioinformatic study suggested that there exist 200-255 miRNAs in humans, accounting for almost 1% of the predicted genes (Lim et al., *Science,* 299, 1540, 2003a). If the prediction is correct, about 100 miRNA genes remain to be identified in humans because 152 miRNAs have been reported, of which 109 miRNAs have been experimentally validated (Brennecke and Cohen, *Genome Biol.,* 4, 228, 2003). miRNAs that are expressed only in specific developmental stages or conditions would be difficult to be cloned or validated. However, miRNAs have not been isolated yet from human embryonic stem cells.

DETAILED DESCRIPTION OF THE INVENTION

Therefore, the object of the present invention is to provide novel miRNAs isolated from human embryonic stem cells and uses thereof.

To achieve the object of the present invention, the present invention provides an isolated nucleic acid molecule, comprising
(a) a nucleotide sequence selected from the group consisting of SEQ ID NOs: 1-17;
(b) a nucleotide sequence which is the complement of (a);
(c) a nucleotide sequence which has an identity of at least 80% to a sequence of (a) or (b); or
(d) a nucleotide sequence which hybridizes under stringent conditions to a sequence of (a), (b) or (c),
wherein the nucleic acid molecule was isolated from human embryonic stem cells, and uses thereof.

The present invention is the first to isolate miRNAs from human embryonic stem cells.

The miRNAs of the present invention may have a nucleotide sequence selected from the group consisting of SEQ ID NOs: 1-17, as shown in the following Table 1.

TABLE 1

Novel miRNAs isolated from human embryonic stem cells

| ID | Sequence | SEQ ID NO |
|---|---|---|
| miR-302b* | ACUUUAACAUGGAAGUGCUUUCU | 1 |
| miR-302b | UAAGUGCUUCCAUGUUUUAGUAG | 2 |
| miR-302c* | UUUAACAUGGGGGUACCUGCUG | 3 |
| miR-302c | UAAGUGCUUCCAUGUUUCAGUGG | 4 |
| miR-302a* | UAAACGUGGAUGUACUUGCUUU | 5 |
| miR-302d | UAAGUGCUUCCAUGUUUGAGUGU | 6 |
| miR-367 | AAUUGCACUUUAGCAAUGGUGA | 7 |
| miR-200c | UAAUACUGCCGGGUAAUGAUGGA | 8 |
| miR-368 | ACAUAGAGGAAAUUCCACGUUU | 9 |
| miR-154* | AAUCAUACACGGUUGACCUAUU | 10 |
| miR-369 | AAUAAUACAUGGUUGAUCUUU | 11 |

TABLE 1-continued

Novel miRNAs isolated from human embryonic stem cells

| ID | Sequence | SEQ ID NO |
|---|---|---|
| miR-370 | GCCUGCUGGGGUGGAACCUGG | 12 |
| miR-371 | GUGCCGCCAUCUUUUGAGUGU | 13 |
| miR-372 | AAAGUGCUGCGACAUUUGAGCGU | 14 |
| miR-373* | ACUCAAAAUGGGGCGCUUUCC | 15 |
| miR-373 | GAAGUGCUUCGAUUUUGGGGUGU | 16 |
| miR-374 | UUAUAAUACAACCUGAUAAGUG | 17 |

The present invention encompasses nucleic acid molecules which are complementary to the nucleotide sequence of miRNA listed in the above table 1. Moreover, a nucleotide sequence which has an identity of at least 80%, preferably of at least 90% and more preferably of at least 95%, to the nucleotide sequence selected from the group of consisting of SEQ ID NOs: 1-17 or the complementary sequence thereof, is included in the present invention. The term "identity" refers to the degree of sequence identity between two nucleic acid sequences, more particularly to the degree that two bases on the same position precisely corresponds to each other in two aligned sequences. The identity can be determined using a identity search program known in the pertinent art such as BLAST FASTA or Smith Waterman Algorithm etc.

Furthermore, the present invention encompasses nucleotide sequences which complementarily bind, that is, hybridize, under stringent conditions, with one selected from the group consisting of the nucleotide sequence of SEQ ID NOs: 1-17; the complementary sequence thereof; and the nucleotide sequence having an identity at least 80% to the sequences. The complementary binding conditions may be general hybridization conditions known in the art. Preferably, it comprises reacting (washing) for 1 h in 1×SSC and 0.1% SDS at 45° C. or 48° C., more preferably, for 1 h in 0.2×SSC and 0.1% SDS at 50° C. Non-hybridized bases are removed during the reacting.

The isolated nucleic acid molecules of the present invention preferably have a length of from 18 to 100 nt (nucleotides), and more preferably from 18 to 100 nt. The mature miRNAs out of the inventive nucleic acid molecules usually have a length of 19-24 nt, particularly 21, 22 or 23 nt. The nucleic acid molecules of the present invention may be also provided as a miRNA precursor molecule (pre-miRNA) which generally has a length of 50-100 nt, preferably 65-95 nt. It should be noted that the miRNA precursor molecule may be produced by processing of a primary transcript which may have a length of >100 nt. The miRNA precursor molecule may have a nucleotide sequence selected from the group consisting of SEQ ID NOs: 84-99, as shown in the following table 2. It preferably has secondary structure as shown in FIG. 2.

TABLE 2

Nucleotide sequences of miRNA precursors of the present invention

| miRNAs | Sequence of miRNA precursors (5'→3') | Size (nt) | SEQ ID NO |
|---|---|---|---|
| miR-302b* and miR-302b | GUUGGGUGGGCUCCCUUCAACUUUAACAUGGAAGUGC UUUCUGUGACUUUAAAAGUAAGUGCUUCCAUGUUUUA GUAGGAGUGAAUCCAAU | 91 | 84 |
| miR-302c* and miR-302c | GGGAUCCCCUUUGCUUUAACAUGGGGGUACCUGCUG UGUGAAACAAAAGUAAGUGCUUCCAUGUUUCAGUGGA GGUGUCUC | 81 | 85 |
| miR-302a* and miR-302a | CCACCACUUAAACGUGGAUGUACUUGCUUU GAAACUAAAGAAGUAAGUGCUUCCAUGUUUUGGUGAU GG | 69 | 86 |
| miR-302d | AGGGGCCCCCUCUACUUUAACAUGGAGGCACUUGCUG UGACAUGACAAAAAUAAGUGCUUCCAUGUUUGAGUGU GGUGGUUCCU | 84 | 87 |
| miR-367 | UGGCUACAGGCCAUUACUGUUGCUAAUAUGCAACUCU GUUGAAUAUAAAUUGGAAUUGCACUUUAGCAAUGGUG AUGGAUUGUUAAGCCA | 90 | 88 |
| miR-200c | GGCGGGGGCCCUCGUCUUACCCAGCAGUGUUUGGGUG CGGUUGGGAGUCUCUAAUACUGCCGGGUAAUGAUGGA GGCCCCUGUC | 84 | 89 |
| miR-368 | UUUGGUAUUUAAAAGGUGGAUAUUCCUUCUAUGUUUA UGUUAUUUAUGGUUAAACAUAGAGGAAAUUCCACGUU UUCAGUAUCAAA | 86 | 90 |
| miR-154 | UACUUGAAGAUAGGUAUCCGUGUUGCCUUCGCUUUAU UUGUGACGAAUCAUACACGGUUGACCUAUUUUUCAGU A | 75 | 91 |
| miR-369 | UUGAAGGGAGAUGACCGUGUUAUAUUCGCUUUAUUGA CUUCGAAUAAUACAUGGUUGAUCUUUUCUCAG | 69 | 92 |
| miR-370 | AGACAGAGAAGCCAGGUCACGUCUCUGCAGUUACACA GCUCACGAGUGCCUGCUGGGGUGGAACCUGGUCUGUC U | 75 | 93 |
| MiR-301 | CUGCUAACGAAUGCUCUGACUUUAUUGCACUACUGUA CUUUACAGCUAGCAGUGCAAUAGUAUUGUCAAAGCAU CUGAAAGCAG | 84 | 94 |
| miR-371 | AGCCUGUGGCACUCAAACUGUGGGGGCACUUUCUGCU CUCUGGUGAAAGUGCCGCCAUCUUUUGAGUGUUACCG CU | 76 | 95 |
| miR-372 | UCACCCUGUGGGCCUCAAAUGUGGAGCACUAUUCUGA UGUCCAAGUGGAAAGUGCUGCGACAUUUGAGCGUCAC CGGUGA | 80 | 96 |
| miR-373* and miR-373 | ACUGGGAUACUCAAAAUGGGGCGCUUUCCUUUUUGU CUGUACUGGGAAGUGCUUCGAUUUUGGGGUGUCCCUG U | 75 | 97 |
| miR-296 | CCCUUCCAGAGGGCCCCCCCCUCAAUCCUGUUGUGCCUA AUUCAGAGGGUUGGGUGGAGGCUCUCCUGAAGGG | 72 | 98 |
| miR-374 | UACAUCGGCCAUUAUAAUACAACCUGAUAAGUGUUAU AGCACUUAUCAGAUUGUAUUGUAAUUGUCUGUGUA | 72 | 99 |

*: The underline represents the nucleotide sequences of miRNAs.

The miRNA precursor molecules may be identified using known methods in the pertinent art, such as, MFOLD program (Zuker et al., Algorithms and Thermodynamics for RNA Secondary Structure Prediction: A Practical Guide. Kluwer Academic Publishing, Dordrecht, The Netherlands, 1999).

The nucleic acid molecules of the present invention may be present in single-stranded or double-stranded form The miRNA is usually a single-stranded molecule, while the pre-miRNA is usually an at least partially self-complementary molecule capable of forming double-stranded portions (e.g. stem- and loop-structures).

The nucleic acid molecules of the present invention may be selected from RNA, DNA or nucleic acid analog molecules, such as sugar- or backbone-modified ribonucleotides or deoxyribonucleotides. It should be noted, however, that the other nucleic analogs, such as peptide nucleic acids (PNA) or locked nucleic acids (LNA), are also suitable.

The nucleic acid molecules of the present invention may be an RNA- or DNA molecule, which contains at least one modified nucleotide analog, i.e. a naturally occurring ribonucleotide or deoxyribonucleotide is substituted by a non-naturally occurring nucleotide. The modified nucleotide analog may be located for example at the 5'-end and/or the 3'-end of the nucleic acid molecule.

Preferred nucleotide analogs are selected from sugar- or backbone-modified ribonucleotides. It should be noted, however, that also nucleobase-modified ribonucleotides, i.e. ribonucleotides containing a non-naturally occurring nucleobase instead of a naturally occurring nucleobase are suitable: for example, uridines or cytidines modified at the 5-position, such as 5-(2-amino)propyl uridine, 5-bromo uridine; adenosines and guanosines modified at the 8-position, such as 8-bromo guanosine; deaza nucleotides, such as 7-deaza-adenosine; O- and N-alkylated nucleotides, e.g. N6-methyl adenosine. In preferred sugar-modified ribonucleotides the 2'—OH group is replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. In preferred backbone-modified ribonucleotides the phosphoester group connecting to adjacent ribonucleotides is replaced by a modified group, such as phosphothioate group. It should be noted that the above modifications may be combined.

The nucleic acid molecules of the present invention may be obtained by chemical synthesis methods or by recombinant methods, such as by enzymatic transcription from synthetic DNA-templates or from DNA-plasmids isolated from recombinant organisms. Typically phage RNA-polymerases are used for transcription, such as T7, T3 or SP6 RNA-polymerases.

The nucleic acid molecules of the present invention may be inserted to a vector by operably linking to an expression control sequence. The expression means transcription and optionally further processing, resulting in a miRNA-molecule or miRNA precursor molecule as described above. The vector is preferably a DNA-vector such as a viral vector or a plasmid. Particularly the vector may be an expression vector suitable for nucleic acid expression in eukaryotic, more particularly mammalian cells.

The viral vector is not limited to, but includes retrovirus, adenovirus, herpes virus and avipox virus. The retroviral vector is constructed so that non-viral proteins can be produced by the viral vector within the infected cells by the elimination or modification of all the virus genes. The main advantages of the retroviral vector for gene therapy lie in the fact that a quantity of genes are transferred into replicative cells, the genes transferred into cell DNA are accurately integrated and continuous infection does not occur after the gene transfection (Miller, A. D., Nature, 1992, 357:455-460). The retroviral vector approved by FDA is constructed using PA317 amphotropic retrovirus package cells (Miller, A. D. and Buttimore, C., Molec. Cell Biol., 6:2895-2902, 1986). As non-retroviral vectors, there is adenovirus as mentioned above (Rosenfeld, M. A., et al., Cell, 68:143-155, 1992; Jaffe, H. A. et al., Nature Genetics, 1:372-378, 1992; Lemarchand, et al., Proc. Natl. Acad. Sci. USA, 89:6482-6486, 1992). The main advantages of the adenovirus lie in the fact that it can transfer a quantity of DNA fragments (36 kb genome) and it is capable of infecting non-replicative cells with a very high titer. Also, the herpes virus can be usefully used for human gene therapy (Wolfe, J. H., et al., Nature Genetics, 1:379-384, 1992). Besides, other known suitable viral vectors can be used.

As the plasmid expression vector that can be used in the present invention, there can be used mammal expression plasmids known in the pertinent art. For example, they are not limited to, but typically include pRK5 (European Patent No. 307,247), pSV16B (International Patent Publication 91/08291 A) and pVL1392 (PharMingen).

The present invention provides diagnostic or therapeutic applications of the inventive nucleic acid molecules. For example, miRNAs may be detected in biological samples, e.g. in tissue sections, in order to determine and classify certain cell types or tissue types or miRNA-associated pathogenic disorders which are characterized by differential expression of miRNA-molecules or miRNA-molecule patterns. Further, the developmental stage of cells may be classified by determining temporarily expressed miRNA-molecules.

MiRNA-302b*, miR-302b, miR-302c*, miR-302c, miR-302a*, miR-203d and miR-367 of the present invention are also expressed in human embryonic carcinoma stem cells. miR-374 is specifically expressed in human cervix epitheloid carcinoma cell line (HeLa). Therefore, the nucleic acid molecules are suitable for therapeutic applications. That is, the nucleic acid molecules may be used as modulators or targets of developmental processes or disorders associated with developmental dysfunctions, such as cancer.

Moreover, the inventive nucleic acid molecules may be used as a modulator of the expression of genes which are at least partially complementary to a nucleic acid molecule selected from the group consisting of SEQ ID NOs: 1-17. Further, miRNA molecules may act as target for therapeutic screening procedures. That is, inhibition or activation of miRNA molecules might modulate a cellular differentiation process such as apoptosis.

Furthermore, the nucleic acid molecules may be used as starting materials for the manufacture of sequence-modified miRNA molecules, in order to modify the target-specificity thereof, such as an oncogene, a multidrug-resistance gene or another therapeutic target gene. The novel engineered miRNA molecules preferably have an identity of at least 80% to the miRNA (starting material) which has a nucleotide sequence selected from the group consisting of SEQ ID NOs: 1-17. Further, miRNA molecules can be modified, in order that they are symmetrically processed and then generated as double-stranded siRNAs which are again directed against therapeutically relevant targets.

Furthermore, miRNA molecules of the present invention may be used for tissue reprogramming procedures, e.g. a differentiated cell line might be transformed by expression of miRNA molecules into a different cell type or a stem cell.

For diagnostic or therapeutic applications, the inventive nucleic acid molecules are preferably provided as a pharmaceutical composition. This pharmaceutical composition comprises as an active agent at least one nucleic acid molecule of the present invention and optionally a pharmaceutically acceptable carrier.

The administration of the pharmaceutical composition may be carried out by known methods, wherein a nucleic acid is introduced into a desired target cell in vitro or in vivo.

Commonly used gene transfer techniques include transient transfection, microinjection, transduction, cell-fusion, calcium phosphate precipitation, liposome-mediated transfection, DEAE dextran-mediated transfection, polybrene-mediated transfection, electroporation, gene gun and viral methods (Wu et al., *J. Bio. Chem.*, 267:963-967, 1992; Wu and Wu, *J. Bio. Chem.*, 263:14621-14624, 1988; Graham et al., *Virol.*, 52:456, 1973; McCutchan et al., *J. Natl. Cancer Inst.*, 41:351, 1968; Chu et al, *Nucl. Acids Res.*, 15:1311, 1987; Fraley et al., *J. Biol. Chem.*, 255:10431, 1980; and Capecchi, *Cell*, 22:479, 1980). A recent addition to this arsenal of techniques for the introduction of DNA into cells is the use of cationic liposomes (Felgner et al, *Proc. Natl. Acad., Sci.*, U. S. A. 84:7413, 1987). Commercially available cationic lipid formulations are e.g. Tfx 50 (Promega) or Lipofectamin 2000 (Life Technologies).

The pharmaceutical composition of the present invention may be in form of a solution, e.g. an injectable solution, a cream, ointment, tablet, suspension or the like. The composition may be administered in any suitable way, e.g. by injection, by oral, topical, nasal, rectal application etc. The carrier may be any suitable pharmaceutical carrier. Preferably, a carrier is used, which is capable of increasing the efficacy of the RNA molecules to enter the target-cells. Suitable examples of such carriers are liposomes, particularly cationic liposomes.

In addition, the present invention provides a marker specific to human stem cells, comprising nucleic acid molecules of the present invention. The human stem cells may be embryonic stem cells, embryonic carcinoma stem cells or adult neural stem cells. Preferably, the embryonic stem cells may be undifferentiated embryonic stem cells. Specifically, out of the nucleic acid molecules of the present invention, the nucleic acid molecule having a nucleotide sequence selected from the group consisting of SEQ ID NOs: 1-10 and SEQ ID NOs: 13-16 is specifically expressed in undifferentiated human embryonic stem cells. Therefore, the nucleic acid molecules can be usefully used as a marker specific to undifferentiated human embryonic stem cells.

The present invention provides also a method for determining the type of stem cells, comprising the steps of:

(a) preparing a RNA sample from the stem cells; and (b) detecting the expression of a nucleic acid molecule having a nucleotide sequence selected from the group consisting of SEQ ID NOs: 1-10 and SEQ ID NOs: 13-16, in the prepared RNA sample.

The preparation of total RNA from stem cells was performed according to a method known in the pertinent art. Preferably, it is performed by using TRIzol reagent (Gibco BRL). The expression of nucleic acid molecules of the present invention in the prepared total RNA sample can be detected by a method known in the pertinent art. It is preferably detected by performing northern blot analysis using the nucleic acid molecules as a probe. As the probe, the nucleic acid having a nucleotide sequence selected from the group consisting of SEQ ID NOs: 37-41, 43-47 and 51-54 can be used.

As described above, the determination of stem cell type can be performed by detecting the expression of one of the nucleic acid molecules using a probe specific to each nucleic acid molecule. As for another method, it may also be performed by detecting the expression of a cluster containing miRNAs that are present on same chromosome. In this case, it is preferably performed by RT-PCR analysis. The primers for RT-PCR analysis may be designed on the basis of nucleotide sequences at both border of the cluster. For example, the expression of a cluster containing nucleic acid molecules that are present on chromosome 4 (miR-302b*~302b~302c*~302c~302a*~302a~302d~367) can be examined. In this case, it may be examined by RT-PCR analysis with a primer set of SEQ ID NOs: 74-75. The expression of a cluster containing nucleic acid molecules that are present on chromosome 19 (miR-371~372~373*~373) can be also examined. In this case, it may be examined by RT-PCR analysis with a primer set of SEQ ID NOs: 76-77.

The inventive method allows to distinguish between human embryonic stem cells and mouse embryonic stem cells, and to select human embryonic stem cells or human embryonic carcinoma stem cells. Especially, for selecting human embryonic stem cells, the expression of a nucleic acid molecule having a nucleotide sequence selected from the group consisting of SEQ ID NOs: 1-7 that is specifically expressed in human embryonic stem cells, or a cluster containing the same (miR-302b*~302b~302c*~302c~302a*~302a~302d~367) can be detected. For selecting human embryonic carcinoma stem cells, it may be performed by detecting the expressions of both (a) a nucleic acid molecule (SEQ ID NOs: 1-7) expressed in human embryonic carcinoma stem cells as well as in human embryonic stem cells, or a cluster containing the same; and (b) a nucleic acid molecule (SEQ ID NOs: 8-10 and 13-16) expressed only in human embryonic stem cells, or a cluster containing the same. That is, when the expression of nucleic acid molecule (a) is detected while the expression of nucleic acid molecule (b) is not detected in RNA sample of stem cells, it is determined as embryonic carcinoma stem cells.

The nucleic acid molecules of the present invention and the methods using the same may be utilized as a key factor to identify differences between proliferation- and differentiation mechanisms in human embryonic stem cells and mouse embryonic stem cells. The present invention may provide a regulator to analyze the embryological mechanisms and developmental patterns in human embryonic stem cells and human embryonic carcinoma stem cells using miRNAs that are differentially expressed in these stem cells.

Moreover, it can be determined whether human embryonic stem cells are differentiated using the nucleic acid molecules of the present invention. Therefore, the present invention provides a method for determining the differentiation of human embryonic stem cells, comprising, (a) preparing a RNA sample from the stem cells; and (b) detecting the expression of a nucleic acid molecule having a nucleotide sequence selected from the group consisting of SEQ ID NOs: 1-10 and SEQ ID NOs: 13-16, in the prepared RNA sample.

The preparation of total RNA from the stem cells and detection of the expression of nucleic acid molecules of the present invention in the prepared total RNA may be performed as described above. The nucleic acid having a nucleotide sequence selected from the group consisting of SEQ ID NOs: 37-41, 43-47 and 51-54 can be used as the probe. The method may be performed by detecting the expression of miRNAs on chromosome 4 (miR-302b*~302b~302c*~302c~302a*~302a~302d~367) or a cluster containing the same, or the expression of miRNAs on chromosome 19 (miR-371, miR-372, miR-373* and miR- 373) or a cluster containing the same, by northern blot analysis or RT-PCR. Most preferably, it may be performed by detecting the expression of miRNAs on chromosome 19 (miR-371, miR-372, miR-373* and miR-373) or the cluster containing the same, by northern blot analysis or RT-PCR.

In the embodiment of the present invention, the present inventors have cloned 36 small RNAs with known characteristics of miRNAs from human embryonic stem cells. 16 miRNAs of them were identical to previously reported miRNAs from various mammalian adult tissues and cell lines. Of the remaining 20 miRNAs, 3 miRNAs are identical to those cloned from mouse embryonic stem cells (Houbaviy et al., Dev. Cell, 5:351-358, 2003). Comparison to the study on mouse embryonic stem cells-specific miRNAs revealed interesting similarities between the two miRNA pools from human and mouse embryonic stem cells. Many of the embryonic stem cells-specific miRNA genes are highly related to each other and organized as clusters. The miR-302b, miR-302c and miR-302d on chromosome 4 appear to be the close homologues of miR-302 that was cloned from mouse embryonic stem cells (Houbaviy et al., Dev. Cell, 5:351-358, 2003).

The present inventor found that there are additional miRNA-like sequences related to miR-302 (see Table 3). Mouse miR-302 and its related sequences also form a gene cluster on mouse chromosome 3. Another set of miRNAs, miR-371, miR-372, miR-373* and miR-373 on chromosome 19, is the human homologues of mouse miR-290, miR-291-s, miR-291-as, miR-292-s, miR-292-as, miR-293, miR-294 and miR-295 expressed in mouse embryonic stem cells (Houbaviy et al., Dev. Cell, 5:351-358, 2003). It is intriguing that two human embryonic stem cells-specific miRNA clusters are conversed in the mouse genome. Although the numbers of the homologous genes are different and the sequences are variable in human and mouse clusters, which may implicate divergence of the conserved regulatory pathways, these conserved miRNAs are likely to play central roles in the regulation of mammalian embryonic stem cells.

It should be noted, however, that a considerable proportion of the cloned miRNAs from human and mouse embryonic stem cells are different from each other. 7 out of 20 miRNAs identified in the present invention do riot have apparent homologues among those cloned from mouse embryonic stem cells. Conversely, 5 out of 15 novel miRNAs from mouse embryonic stem cells (Houbaviy et al., Dev. Cell, 5:351-358, 2003) do not have related nucleotide sequences of the present invention. These results may implicate fundamental differences between the regulatory networks in human and mouse embryonic stem cells.

In another embodiment of the present invention, the expression patterns of 36 miRNAs cloned from human embryonic stem cells were examined The miRNAs isolated from human embryonic stem cells can be classified into four groups.

(1) miRNAs that are expressed in human embryonic stem cells as well as in human embryonic carcinoma stem cells; miR-302b*, miR-302b, miR-302c*, miR-302c, miR-302a*, miR-302a, miR-302d and miR-367 (shadowed in bright gray in Table 2 and FIG. 2). These miRNAs may have conserved roles in mammalian pluripotent stem cells. All the other miRNAs, except for miR-302a, are novel miRNAs that are newly provided by the present invention.

(2) miRNAs that are expressed specifically in human embryonic stem cells but not in other cells including human embryonic carcinoma stem cells; miR-200c, miR-368, miR-154*, miR-371, miR-372, miR-373* and miR-373 (shadowed in dark gray in Table 3 and FIG. 2). These miRNAs may have functions specific to human embryonic stem cells. It would be interesting to dissect the molecular basis for the differences between the two pluripotent stem cells; human embryonic stem cells and human embryonic carcinoma stem cells. All these miRNAs are novel miRNAs that are newly provided by the present invention.

(3) miRNAs that are rare in human embryonic stem cells but abundant in HeLa and STO cells; let-7a, miR-301, miR-374, miR-21, miR-29b and miR-29. Only miR-374 out of these miRNAs is novel miRNA which is newly provided by the present invention. These stage-specific miRNAs may play roles in the regulation of development and differentiation, like let-7 in C. elegans.

(4) The last class consists of miR-16, miR-17-5p, miR-19b, miR-26a, miR-92, miR-103, miR-130a and miR-222. These are expressed in most tested cell lines so they may contribute to basic cellular functions (see FIG. 2).

Specially, of miRNAs provided in the present invention, miR-200c, miR-368, miR-154*, miR-302b*~302b~302c*~302c~302a*~302a~302d~367 cluster on chromosome &n 4 &l and miR-&n 372~372~373*~373 cluster on chromosome 19 are expressed specifically in undifferentiated human embryonic stem cells (see FIG. 2 and FIG. 4). The expression pattern of the miRNA cluster on chromosome 19 is particularly interesting. The expression of this cluster becomes evident more rapidly than that of Oct4, which is the earliest marker for human embryonic stem cells known so far (see FIG. 4), and it is detected only during undifferentiation of embryonic stem cells. Also, when their differentiation is started, it is rapidly decreased. Thus, it is tempting to speculate that these miRNAs may be the primary regulators of embryonic stem cell maintenance or differentiation, which act before other known factors including Oct4. These miRNAs may define the very early stage of embryonic development that has not been recognized before.

Moreover, the present inventors found that the expression of miR-371~372~373*~373 cluster (chromosome 19) and miR-302b*~302b~302c*~302c~302a*~302a~302d~367 cluster (chromosome 4) were detected in human adult neural stem cells (see FIG. 6). These miRNAs molecules may be involved in regulatory mechanisms of proliferation and differentiation of human adult neural stern cells.

For most miRNAs, RNA from only one side of the miRNA precursor is typically cloned or detected on Northern blot. In the present invention, four miRNA genes (miR-302b, miR-302c, miR-302a and miR-373 hairpins) yielded small RNAs corresponding to both strands of the stems (see Table 3 and FIG. 1). However, the frequencies of clones of the two opposite strands are not equal, indicating that there is a certain degree of asymmetry in the abundance of these miRNAs. In the case of miR-302b and miR-302c, the ratios between the cloning frequencies of the two sides were 22.5:1 and 10:1, respectively. According to the standard nomenclature (Ambros et al., RNA, 9:277-279, 2003), the less abundant miRNA of each pair was designated with an asterisk mark. Recent studies using siRNA duplexes demonstrated that this asymmetry comes from asymmetric degradation of the opposing strand following Dicer processing. According to this, the strand with the less stable 5' end has a better chance to survive (Khvorova et al., Cell, 11 5:209-216, 2003; Schwarz et al., Cell, 115:199-208, 2003). Sixty-nine percent of novel miRNA precursors provided by the present invention are clearly in agreement with this, indicating that this rule is generally valid although the mechanism of strand selection for miRNA may be more complex than that for siRNA.

BRIEF DESCRIPTION OF THE FIGURES

FIG. 3 shows multiple sequence alignment of the genomic DNA segments corresponding to the miRNA clusters of the present invention. The positions of dominantly expressed mature miRNAs are shown in box and the positions of weakly expressed mature miRNAs are underlined. Conserved residues are indicated with asterisks.

FIG. 5 is schematically depicted genomic organization of miRNA gene clusters of the present invention.

EXAMPLES

Figure 1:
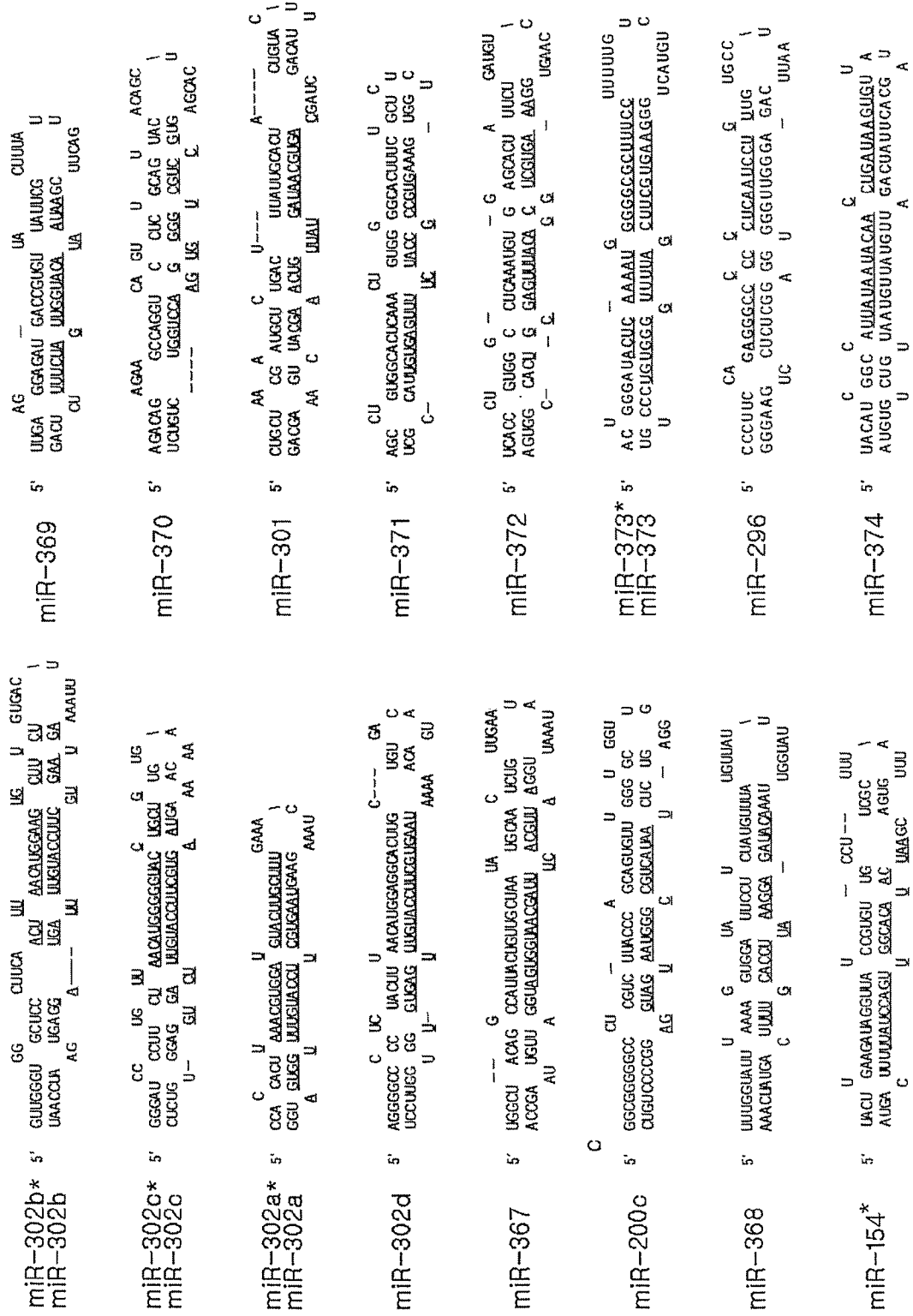
FIG. 1 shows predicted structures of miRNA precursors. RNA secondary structure prediction was performed using MFOLD (version 3.1) and manually refined to accommodate G/U wobble base pairs in the helical segments. The miRNA sequences are underlined.

The present invention will be further described in detail by the examples.

However, the following examples solely illustrate the invention; the matter of the invention should not be construed to be limited thereto.

Reference Example 1

Culture of Embryonic Stem Cells

Human embryonic stem cells, SNU-hES3 (Seoul National University, Korea) and MIZ-hES1 (Mizmedi hospital, Korea) were maintained in DMEM/F12 (Gibco BRL) supplemented with 20% (v/v) serum replacements (Gibco BRL), penicillin (100 IU/ml, Gibco BRL) and streptomycin (100 μg/ml, Gibco BRL), 0.1 mM nonessential amino acids (NAA, Gibco BRL), 0.1 mM Mercaptoethanol (Sigma) and 4 ng/ml basic FGF (R&D). Media were changed daily. Human embryonic stem cell colonies were cultured on a feeder layer of mouse STO (ATCC CRL-1503) cells pre-treated with mitomycin C (Sigma) and were manually detached and transferred onto new STO feeders every 5-6 days. HS-3 mouse embryonic stem cells (Postech) were grown under standard condition (Evans and Kaufman, *Nature*, 292: 154-156, 1981).

Reference Example 2

Differentiation of Human Embryonic Stem Cells

To prepare embryoid bodies (EBs), whole colonies of human embryonic stem cells were detached by glass pipette, transferred onto petri-dishes coated with pluronic F-127 (Sigma), and incubated for 10 days. The media for EB were identical to the media for human embryonic stem cell except that it lacked bFGF. Every two days, media were changed using a pipette. To further differentiate EBs made from SNU-hES3, they were plated onto tissue culture plates coated with poly-L-ornithin (0.01% (v/v))/fibronectin (5 g/ml (w/v)). Cells were further incubated for 5 days in N2 supplement medium containing 20 ng/ml bFGF and the medium was changed daily. Confluent cells were manually detached, and then pipetted using yellow tips and transferred onto new plates coated with poly-L-ornithin/fibronectin. Cells were cultured for 5 days in N2 medium containing 20 ng/ml bFGF. When the cells reached confluency, they were trypsinized and split 2:1 or 3:1 at new poly-L-ornithin/fibronectin-cotated plates.

Example 1 miRNAs Cloning from Human Embryonic Stem Cells

<1-1> cDNA Library Construction from Human Embryonic Stem Cells and Culture Thereof To identify miRNAs expressed in human embryonic stem cells, two independent cDNA libraries were constructed. Total RNA was prepared from each cell line with TRIzol reagent (Gibco BRL). The cDNA libraries were then constructed by directional cloning method using size fractionated RNA (17-26 nt) from undifferentiated human embryonic stem cells (SNU-hES-3, registered at the Korea Stem Cell Research Center) (Lagos-Quintana et al. *Science*, 294: 853-858, 2001). To validate the undifferentiating status of the human embryonic stem cell, SNU-hES3, the steady-state level of Oct4 mRNA was determined by RT-PCR. The RT-PCR was performed by following method: the first-strand cDNA from the indicated cells was synthesized with SUPER-SCRIPT (Gibco BRL) using 2-5 μg of total RNA. The PCR was performed using primers of SEQ ID NO: 37 and 38. To assess the undifferentiating status of the human embryonic stem cells, the expressions of alkaline phosphatase (AP) and the developmental stage-specific embryonic antigens (embryonic cell surface markers), SSEA-1, SSEA-3 and SSEA-4 were checked by immunostaining. As a result, SNU-hES3 cells expressed a high level of Oct4, AP, SSEA-3, and SSEA-4 (data not shown). From the result, it was validated that the undifferentiating status of SNU-hES3 cells were maintained.

<1-2> MiRNAs Cloning from Human Embryonic Stem Cells and Bioinformatics Analysis MiRNAs were cloned from the cDNA libraries constructed in the Example <1-1> using the method of Lagos-Quintana et al. (Lagos-Quintana et al., *Science*, 294: 853-858, 2001). Database searches of the cloned miRNAs were performed at the BLAST server (Altschul et al., *J. Mol. Biol.* 215:403-410, 1990) and ENSEMBL server (Hubbard et al., *Nucleic Acids Res.*, 30:38-41, 2002). Sequence alignment between miRNA sequences were performed by using CLUSTALW (Higgins and Sharp, *Dev. Cell*, 5:351-358, 1988).

As a result, sequences were obtained for 1,475 small cDNAs that resulted in 733 non-redundant sequences. Approximately 70% of these sequences corresponded to the expressed strand of loci that encode longer, previously identified coding or noncoding RNAs such as tRNAs and rRNAs.

To distinguish miRNAs from degradation products or small interfering RNAs (siRNAs), the present inventors evaluated the ability of RNA containing the clones to fold into stem-loop, that is, the secondary structure of the RNA by using the MFOLD program (Zuker et al., Algorithms and Thermodynamics for RNA Secondary Structure Prediction: A Practical Guide. Kluwer Academic Publishing, Dordreclht, The Netherlands, 1999). Thirty-six RNAs were found in the stems of strong hairpin structures (see below Table 1 and FIG. 1).

TABLE 3

The miRNAs cloned from human embryonic stem cells.

| ID[a] | Sequence[b] | Observation[c] 1st | Observation[c] 2nd | Size (nt) | Chromosome | Conservation[d] | Expression[e] | SEQ ID NO. |
|---|---|---|---|---|---|---|---|---|
| miR-302b* | ACUUUAACAUGGAAGUGCUUUCU | 1 | 1 | 23 | 4 | Mm | 00011 | 1 |
| miR-302b | UAAGUGCUUCCAUGUUUUAGUAG | 9 | 36 | 23 | 4 | Mm | 00011, 000221 | 2 |
| miR-302c* | UUUAACAUGGGGGUACCUGCUG | 1 | | 22 | 4 | Mm | 00011 | 3 |
| miR-302c | UAAGUGCUUCCAUGUUUCAGUGG | 7 | 3 | 23 | 4 | Mm | 00012 | 4 |
| miR-302a* | UAAACGUGGAUGUACUUGCUUU | 3 | 3 | 22 | 4 | Mm | 00012 | 5 |
| miR-302a | UAAGUGCUUCCAUGUUUUGGUGA | 6 | 17 | 23 | 4 | Mm, Rn | 00023, 001223 | 18 |
| miR-302d | UAAGUGCUUCCAUGUUUGAGUGU | 1 | 12 | 23 | 4 | Mm | 00023, 000112 | 6 |
| miR-367 | AAUUGCACUUUAGCAAUGGUGA | 2 | 3 | 22 | 4 | Mm, Rn | 00011 | 7 |
| miR-200c | UAAUACUGCCGGGUAAUGAUGGA | | 4 | 23 | 12 | Mm | 00010, 000110 | 8 |
| miR-368 | ACAUAGAGGAAAUUCCACGUUU | 1 | | 22 | 14 | Mm | 00010, 000110 | 9 |
| miR-154* | AAUCAUACACGGUUGACCUAUU | | 1 | 22 | 14 | Mm | 000110 | 10 |
| miR-369 | AAUAAUACAUGGUUGAUCUUU | 1 | | 21 | 14 | Mm | no signal | 11 |
| miR-370 | GCCUGCUGGGGUGGAACCUGG | | 1 | 21 | 14 | Mm | 00S000 | 12 |
| miR-301 | CAGUGCAAUAGUAUUGUCAAAGC | 1 | | 23 | 17 | Mm, Rn, Fr | 21111 | 19 |
| miR-371 | GUGCCGCCAUCUUUUGAGUGU | | 2 | 21 | 19 | Mm | 002120 | 13 |
| miR-372 | AAAGUGCUGCGACAUUUGAGCGU | | 1 | 23 | 19 | Mm | 000230 | 14 |
| miR-373* | ACUCAAAAUGGGGGCGCUUUCC | | 1 | 22 | 19 | Mm | 00SSS0 | 15 |
| miR-373 | GAAGUGCUUCGAUUUUGGGGUGU | | 1 | 23 | 19 | Mm | 000120 | 16 |
| miR-296 | AGGGCCCCCCCUCAAUCCUGU | | 1 | 21 | 20 | Mm | 00SSS | 20 |
| miR-374 | UUAUAAUACAACCUGAUAAGUG | 2 | | 22 | X | Mm | 11000 | 17 |
| Sum | | 35 | 87 | | | | | |
| let-7a-1 | UGAGGUAGUAGGUUGUAUAGUU | | 1 | 22 | 9, 11, 17, 22 | | 33000 | 21 |
| miR-16 | UAGCAGCACGUAAAUAUUGGCG | | 2 | 22 | 13 | | 22112 | 22 |
| miR-17-5p | CAAAGUGCUUACAGUGCAGGUAGU | | 1 | 24 | 13 | | 11112 | 23 |
| miR-19b | UGUGCAAAUCCAUGCAAAACUGA | 7 | 1 | 23 | 13, X | | 111111 | 24 |
| miR-21 | UAGCUUAUCAGACUGAUGUUGAC | | 4 | 23 | 17 | | 32111 | 25 |
| miR-26a | UUCAAGUAAUCCAGGAUAGGCU | | 3 | 22 | 3 | | 221112 | 26 |
| miR-29 | CUAGCACCAUCUGAAAUCGGUU | | 1 | 22 | 7 | | 12SSSS | 27 |
| miR-29b-2 | UAGCACCAUUUGAAAUCAGUG | | 1 | 21 | 7 | | 11000 | 28 |
| miR-92 | UAUUGCACUUGUCCCGGCCUG | 1 | 1 | 21 | 13, X | | 11112 | 29 |
| miR-103 | AGCAGCAUUGUACAGGGCUAUG | 1 | 2 | 22 | 5 | | 21112 | 30 |
| miR-124a # | UUAAGGCACGCGGUGAAUGCCA | 3 | 1 | 22 | 8 | | 00SSS | 31 |
| miR-130a # | CAGUGCAAUGUUAAAAGGGCAU | | 1 | 22 | 11 | | 12223 | 32 |

TABLE 3-continued

The miRNAs cloned from human embryonic stem cells.

| ID[a] | Sequence[b] | Observation[c] 1st | Observation[c] 2nd | Size (nt) | Chromosome | Conservation[d] some | Expression[e] sion | SEQ ID NO. |
|---|---|---|---|---|---|---|---|---|
| miR-134 # | UGUGACUGGUUGACCAGAGGGG | 1 | | 22 | 14 | | 00SSS0 | 33 |
| miR-135-2 # | UAUGGCUUUUUAUUCCUAUGUGA | | 1 | 23 | 12 | | no signal | 34 |
| miR-136 # | ACUCCAUUUGUUUUGAUGAUGGA | 1 | | 23 | 14 | | no signal | 35 |
| miR-222 | AGCUACAUCUGGCUACUGGGUCUC | 1 | 1 | 24 | X | | 11SSS1 | 36 |
| sum | | 15 | 21 | | | | | |

Figure 2:
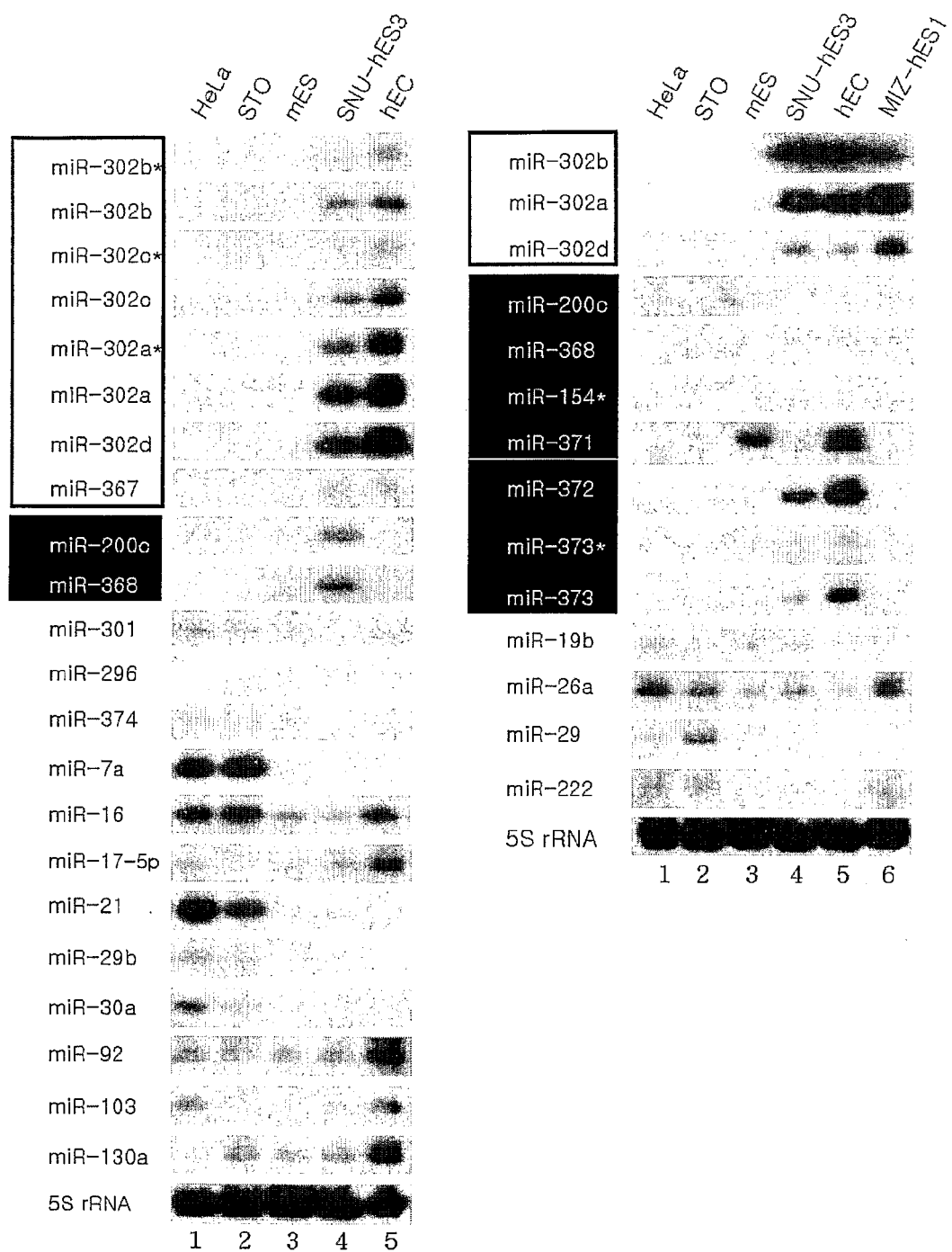
FIG. 2 is northern blot analysis results of miRNAs cloned from human embryonic stem cells. MiRNAs expressed in embryonic stem cells as well as in embryonic carcinoma stem cells are shadowed in bright gray with black border, while miRNAs expressed specifically in embryonic stem cells are shadowed in black.

[a]miRNAs that were newly identified in the present invention are listed in the upper panel. The shadow in bright gray indicates the miRNAs expressed in both ES cells (embryonic stem cells) and EC cells (embryonic carcinoma stem cells). The shadow in dark gray indicates the miRNAs expressed in ES cells but not in other cells including EC cells.
[b]The longest clone is presented.
[c]Number of the clones found in each library.
[d]The presence of homologous stem loops in the mouse (Mm), rat (Rn) and pufferfish (Fr) is indicated. Note that these homologues are only predicted ones based on the genomic sequences.
[e]Expression patterns determined by Northern blot analysis. Single digit numbers indicate the relative band intensities of given miRNA in different cell lines as shown in FIG. 2 and do not give information about the relative levels of different miRNAs. Five digits represent band intensities from HeLa, STO, mES, SNU-hES1, and hEC, consecutively. Six digits represent band intensities from HeLa, STO, mES, SNU-hES1, Miz-hES3, and hEC, consecutively. S indicates a smear around approximately 22 nt that makes it difficult to judge the expression level of the given miRNA.

Of the 36 cloned RNAs listed in the above Table 3, 16 were identical to previously reported miRNAs from various mammalian adult tissues and cell lines (Table 3, lower panel). Interestingly, the remaining 20 RNAs were represented by the majority (77%) of the clones (122 of 158 clones) (Table 3, upper panel). This presents a striking contrast to a recent study using a similar cloning method, where 91% of approximately 600 clones matched previously identified miRNAs (Lagos-Quintata et al., RNA, 9:175-179, 2003). The primary difference was in the source of RNA. That is, Lagos-Quintata et al extracted RNAs from various tissues of 18.5-week-old adult mice and the human osteoblast sarcoma cell line Saos-2 (Lagos-Quintata et al., RNA, 9:175-179, 2003), whereas the present inventors extracted RNAs from human embryonic stem cells.

From the above results, it could be confirmed that human embryonic stem cells are highly enriched with a distinct set of miRNAs unlike the cells in adult tissues or other cell lines.

It was investigated that 3 miRNAs of the remaining 20 miRNAs corresponded to 3 miRNAs which were recently identified from mouse embryonic stem cells (Houbaviy et al., Dev. Cell, 5:351-358, 2003): miR-296 (miR-296), miR-301 (miR-301) and miR-302 (miR-302a). Thus, 17 miRNAs cloned from human embryonic stem cells in the present invention are novel (see the above Table 1).

Example 2

The Specific Expression Analysis of Novel miRNAs in Human Embryonic Stem Cells

To validate the expression of the miRNAs cloned in Example 1, Northern blot analysis was performed using total RNAs from undifferentiated human embryonic stem cells (SNU-hES3, Seoul Nation University), mouse embryonic stem cells (HS-3, Postech) and the human embryonic carcinoma stem cell line (NTERA2, ATCC, CRL-1973, USA).

To confirm the expression of miRNAs from human embryonic stem cells, the present inventors employed another human embryonic stem cell line, MIZ-hES1 (Mizmedi hospital, Korea), that is registered in the NIH Human Embryonic Stem Cell Registry. As negative controls, total RNAs from human cervical carcinoma cell line, HeLa cells and mouse fibroblast cell line, STO feeder cells were used.

Total RNA (100 µg) from each cell line was loaded on a 12.5% denaturing polyacrylamide gel. The resolved RNA was transferred to a Zeta-Probe GT blotting membrane (Bio-Rad) for about 12 h. Oligodeoxinucleotides labeled at the 5' end with $^{32}$P-x-ATP were used as probes. Prehybridization and hybridization were carried out using Express Hyb Hybridization Solution (Clontech). The used probes are shown in Table 4 below.

TABLE 4

The probes used in Northern blot analysis

| Probe | Sequence (5'→3') | SEQ ID NO. |
|---|---|---|
| miR-302b* | AGAAAGCACTTCCATGTTAAAGT | 37 |
| miR-302b | CTACTAAAACATGGAAGCACTTA | 38 |
| miR-302c* | CAGCAGGTACCCCCATGTTAAA | 39 |
| miR-302c | CCACTGAAACATGGAAGCACTTA | 40 |
| miR-302a* | AAAGCAAGTACTACCACGTTTA | 41 |
| miR-302a | TCACCAAAACATGGAAGCACTTA | 42 |
| miR-302d | ACACTCAAACATGGAAGCACTTA | 43 |

TABLE 4-continued

The probes used in Northern blot analysis

| Probe | Sequence (5'→3') | SEQ ID NO. |
|---|---|---|
| miR-367 | TCACCATTGCTAAAGTGCAATT | 44 |
| miR-200c | TCCATCATTACCCGGCAGTATTA | 45 |
| miR-368 | AAACGTGGAATTTCCTCTATGT | 46 |
| miR-154* | AATAGGTCAACCGTGTATGATT | 47 |
| miR-369 | AAAGATCAACCATGTATTATT | 48 |
| miR-370 | CCAGGTTCCACCCCAGCAGGC | 49 |
| miR-301 | GCTTTGACAATACTATTGCACTG | 50 |
| miR-371 | ACACTCAAAAGATGGCGGCAC | 51 |
| miR-372 | ACGCTCAAATGTCGCAGCACTTT | 52 |
| miR-373 | ACACCCCAAAATCGAAGCACTTC | 53 |
| miR-373* | GGAAAGCGCCCCCATTTTGAGT | 54 |
| miR-296 | ACAGGATTGAGGGGGGGCCCT | 55 |
| miR-374 | CACTTATCAGGTTGTATTATAA | 56 |
| let-7a-1 | ACTATACAACCTACTACCTCA | 57 |
| miR-16 | CGCCAATATTTACGTGCTGCTA | 58 |
| miR-17-5p | ACTACCTGCACTGTAAGCACTTTG | 59 |
| miR-19b | TCAGTTTTGCATGGATTTGCACA | 60 |
| miR-21 | GTCAACATCAGTCTGATAAGCTA | 61 |
| miR-26a | AGCCTATCCTGGATTACTTGAA | 62 |
| miR-29 | AACCGATTTCAGATGGAGCTAG | 63 |
| miR-29b-2 | CACTGATTTCAAATGGTGCTA | 64 |
| miR-92 | CAGGCCGGGACAAGTGCAATA | 65 |
| miR-103 | CATAGCCCTGTACAATGCTGCT | 66 |
| miR-124a # | TGGCATTCACCGCGTGCCTTAA | 67 |
| miR-130a # | ATGCCCTTTTAACATTGCACTG | 68 |
| miR-134 # | CCCCTCTGGTCAACCAGTCACA | 69 |
| miR-135-2 # | TCACATAGGAATAAAAAGCCATA | 70 |
| miR-136 # | TCCATCATCAAAACAAATGGAGT | 71 |
| miR-222 | GAGACCCAGTAGCCAGATGTAGCT | 72 |

As shown in FIG. 2, of the 17 newly identified miRNAs in the present invention, 14 miRNAs except for miR-369, miR-370 and miR-374, were specifically expressed in a human embryonic stem cell-specific manner; miR-302b*, miR-302b, miR-302c*, miR-302c, miR-302a*, miR-302d, miR-367, miR-200c, miR-368, miR-154*, miR-371, miR-372, miR-373* and miR-373. Of them, miR-302b*, miR-302b, miR-302c*, miR-302c, miR-302a*, miR-302d and miR-367 were expressed both in human embryonic stem cells and in human embryonic carcinoma stem cells. On the other hands, miR-200c, miR-368, miR-154*, miR-371, miR-372, miR-373* and miR-373 were specifically expressed in human embryonic stem cells. Of the remaining 3 clones, miR-374 was mainly expressed in HeLa and STO cell lines. MiR-369 and miR-370 could not be detected. They might be expressed only at very low levels (data not shown).

It could be confirmed that most of miRNAs provided by the present invention are specifically expressed in human embryonic stem cells. Meanwhile, miR302a that was previously reported in mouse embryonic stem cells as miR-302 (Houbaviy et al., Dev. Cell, 5:351-358, 2003) was also expressed specifically in mouse embryonic stem (mES) cells, human embryonic stem (hES) cells and human embryonic carcinoma stem (hEC) cells. MiR-296 (miR-296), previously cloned from mouse embryonic stem cells, appeared as smear that made it difficult to judge the specificity of expression. MiR-301 was detectable in the all samples tested.

Example 3

Gene Cluster Analysis of miRNA Gene

Genomic loci for 12 miRNAs cloned in the Example 1 were found in two gene clusters.

Eight miRNA loci (miR-302b, miR-302b*, miR-302c, miR-302c*, miR-302a, miR-302a*, miR-302d and miR-367) are located within an about 700 bp region on chromosome 4. Of the above eight miRNA genes, the remaining miRNAs except for miR-302a are novel miRNAs provided by the present invention. Another four miRNAs (miR-371, miR-372, miR-373 and miR-373*) are found within a 1050 bp region on chromosome 19. Sequence comparison of these miRNAs shows that the miRNAs in a given cluster are highly related (see FIG. 3).

Especially, four miRNAs from chromosome 4 cluster (miR-302b, miR-302c, miR302a (miR-302) and miR-302d) are highly homologous to each other. Their sequence similarity is greatest in the 5' portions of the miRNA sequences as is the case with the lin-4 and let-7 families. This finding is consistent with the hypothesis that target recognition occurs primarily via 5' sequences (Lai, Nat. Gent., 30:363-364, 2002). These related miRNAs may recognize a consensus target sequence and hence act on the same mRNAs or different mRNAs with conserved binding sites. Therefore, recognition of these miRNA gene families should help in the identification of putative mRNA targets. The consensus sequence for these clustered miRNAs is 5'-UAAGUGCUUCCAUG-UULNNGUNN-3' (SEQ ID NO: 73) (see FIG. 3A). While these miRNAs are the most abundant ones in human embryonic stem cells, their murine homologue miR-302 appears to be less abundant in mouse embryonic stem cells (Houbaviy et al., Dev. Cell, 5:351-358, 2003). Interestingly, additional sequences related to this family are found in mouse chromosome 3 (see Table 3). Three putative mouse homologues form stem-loop structures and are in a gene cluster.

Of miRNAs provided by the present invention, miR-371, miR-372 and miR-373 are also found in a cluster on chromosome 19 (see FIG. 3B). Of miRNAs predicted by Houbaviy et al., miR-290, miR-291-s, miR-291-as, miR-292-s, miR-292-as, miR-293, miR-294 and miR-295 have sequence similarity to human miRNAs and are expressed in mouse embryonic stem cells. Mouse miR-291-295 are located as one cluster spanning 2.2 kb (Houbaviy et al., Dev. Cell, 5:351-358, 2003).

It is noted that the miRNAs from the two gene clusters, for instance, miR-302a/miR-302 on chromosome 4 and miR-372 on chromosome 19, are similar to some extent, implicating that they may have originated from a common ancestral miRNA gene.

Example 4

Expression Pattern Analysis of miRNAs in Human Embryonic Stem Cell Differentiation To examine the expression patterns of the miRNAs during differentiation of human embryonic stem cell, RT-PCR was carried out. Because clustered miRNA genes are generally transcribed into pri-miRNAs (polycistronic primary transcripts) (Lee et al, *EMBO J.*, 21:4663-4671, 2002), the primers were chosen to bind outside the boundary of the predicted approximately 70 nt stem-loop clusters so that the present inventors could detect pri-miRNAs covering the entire cluster. The primers used in RT-PCR analysis are shown in Table 5 below.

TABLE 5

The primers used in RT-PCR analysis

| miRNA gene cluster | Primer | Sequence (5'→3') | SEQ ID NO. |
|---|---|---|---|
| miR-302b*~302b~302c*~302c~302a*~302a~302d~367 | Forward | GGGCTCCCTTCAACTTTAAC | 74 |
| | Reverse | ATTCTGTCATTGGCTTAACAATCCATCACC | 75 |
| miR-371~372~373*~373 | Forward | CGATCGCCGCCTTGCCGCAT | 76 |
| | Reverse | TGGTTCGTGATGCCCTACTCAAACAGGGAC | 77 |
| miR-30a~30a* | Forward | ATTGCTGTTTGAATGAGGCTTCAGTACTTT | 78 |
| | Reverse | TTCAGCTTTGTAAAAATGTATC AAGAGAT | 79 |
| let-7a-1 | Forward | GATTCCTTTTCACCATTCACCCTGGATGTT | 80 |
| | Reverse | TTTCTATCAGACCGCCTGGATGCAGACTTT | 81 |
| GAPDH | Forward | TGTCATCAATGGAAATCCCATCACC | 82 |
| | Reverse | CATGAGTCCTTCCACGATACCAAA G | 83 |

Total RNA was extracted from the human embryonic stem cell lines (SNU-hES3 and Miz-hES1), EBs (embryoid bodies) derived from each cell line (SNU-hES3(EB) and Miz-hES1(EB)), differentiated cells (SNU-hES3 (Dif)) derived from EBs, and Hela cell, respectively. Preparation of EBs from human embryonic stem cell lines was performed as used in Reference Example 2. RT-PCR was then performed according to the same method as used in Example 1 using the primers in Table 5 above.

As a result, PCR products of the expected size (707 and 1056 bp, respectively) were detected from two human embryonic stem cell lines (see FIG. 4, lanes 2 and 5), indicating that these clusters are indeed single transcriptional units. The steady-state levels of primary transcripts from the two gene clusters decreased when human embryonic stem cells developed into EBs (see FIG. 4, lanes 3 and 6). The expression levels were reduced further in differentiated cells derived from EBs (see FIG. 4, lane 4). These results demonstrate that the clustered miRNAs are expressed specifically in human embryonic stem cells and are rapidly down-regulated during differentiation.

Figure 4:
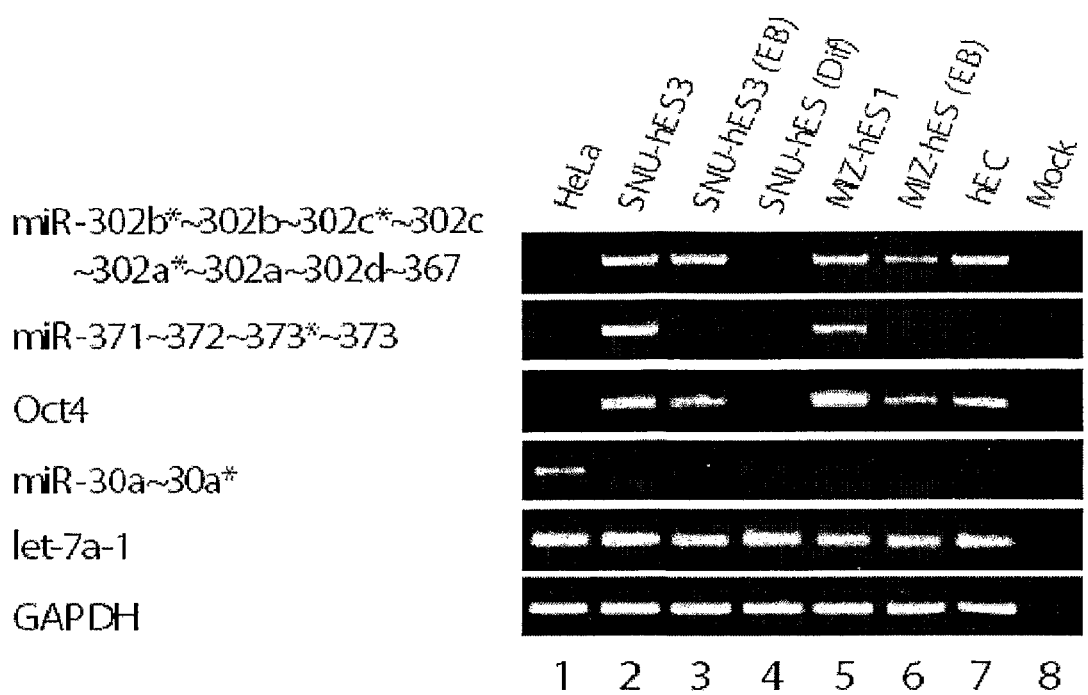
FIG. 4 is RT-PCR analysis results of the specific expression of the miRNA clusters of the present invention in undifferentiated human embryonic stem cells.

To assess the degree of differentiation, the present inventors determined the steady-state levels of Oct4 mRNAs at differential stages by RT-PCR according to the same method as used in Example 1 (see FIG. 4). Interestingly, down-regulation of chromosome 19 cluster (miRNA-371-372-373-373*) precedes that of Oct4. The polycistronic transcripts from the chromosome 4 cluster, but not those from the chromosome 19, were detected in human embryonic carcinoma stem cells (see FIG. 4, lane 7), which is consistent with the results from Northern blot analysis (see FIG. 2).

The control miRNA (miR-30a), which had not been cloned from human embryonic stem cells, was detected in HeLa cells but only barely shown in other cells in accordance with Northern results of Example 2 (see FIGS. 2 and 4). Meanwhile, pri-let-7a-1 transcript was expressed in all of the tested cell lines, although mature let-7a-1 appeared only in HeLa and STO cell lines, as shown in FIG. 2, which suggests that the processing of let-7a-1 may be regulated posttranscriptionally. It would be of great interest to understand how the expression of miRNAs is regulated during development.

Example 5

Expression Analysis of miRNAs in Human Adult Neural Stem Cells

<5-1> Culture of Adult Neural Stem Cells

The cells obtained from the periventricular zone of 8-12 weeks old embryo telencephalon were stably cultured and suspended at concentration of $5\times10^5$ cells/ml. The cell suspension was cultured in a tissue-culture dish. For media, DMEM/F12 as a basal medium and N2 medium supplemented with bFGF (10-20 μg/ml), heparin (8 μg/ml) and EGF (10-20 μg/ml) were used. Every 5 days, media were changed.

<5-2> RT-PCR Analysis

Total RNA was prepared from human adult neural stem cells (hNSC) prepared in the above Example <5-1> and the human embryonic stem cell line (Miz-hES1), respectively. To validate the expression of cluster containing miRNAs of the present invention (miR-302b*~302b~302c*~302c~302a*~302a~302d~367 and miR-371~372~373*~373), RT-PCR analysis was performed using a primer set (SEQ ID NO: 74/75 and 76/77, respectively) as used in Example 1. The expression of β-actin was validated as a control.

Figure 6:
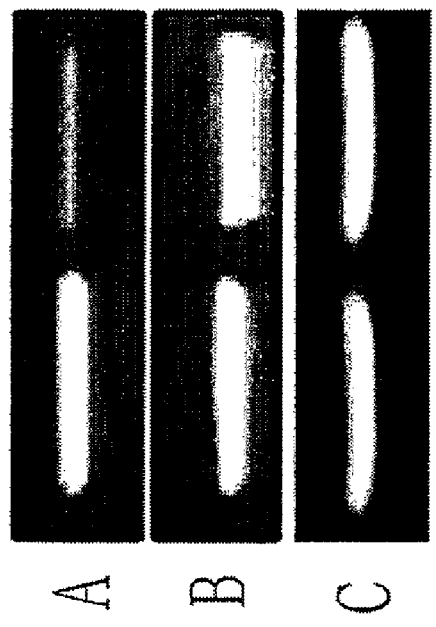
FIG. 6 is RT-PCR analysis results of the specific expression of the miRNA clusters of the present invention in human adult neural stem cells.

As shown in FIG. 6, miR-302b*~302b~302c*~302c~302a*~302a~302d~367 cluster on chromosome 4 and miR-371~372~373*~373 cluster on chromosome 19 were expressed specifically in human adult neural stem cell (hNSC) as well as human embryonic stem cell. It suggests that miRNAs of the present invention play a part in regulatory mechanism of proliferation and differentiation in human adult neural stem cells as well as of human embryonic stem cells.

INDUSTRIAL APPLICABILITY

As described above, the novel miRNAs were cloned from human stem cells in the present invention. The miRNA molecules provided by the present invention can be usefully used as a molecular marker for early developmental stages of undifferentiated human embryonic stem cells. Also, the miRNA molecules of the present invention may play an important role in the regulation of mammalian embryonic stem cells. Therefore, the miRNA molecules can be used for analyzing regulatory networks of human embryonic stem cells.

What is claimed is:

1. An isolated nucleic acid molecule, comprising:
   (a) a nucleotide sequence selected from the group consisting of SEQ ID NO: 1-6; or
   (b) a nucleotide sequence which is the full-length complement of (a); wherein the nucleic acid molecule was isolated from human embryonic stem cells.

2. The nucleic acid molecule of claim 1, wherein the nucleic acid molecule is a miRNA molecule or an analog thereof.

3. The nucleic acid molecule of claim 1, wherein the nucleic acid molecule is a miRNA precursor molecule.

4. The nucleic acid molecule of claim 3, wherein the nucleic acid molecule has a nucleotide sequence selected from the group consisting of SEQ ID NO: 84-87.

5. A vector comprising the nucleic acid molecule of claim 1.

6. A pharmaceutical composition comprising the nucleic acid molecule of claim 1 as an effective component.

7. The pharmaceutical composition of claim 6, which is for diagnostic applications.

8. The pharmaceutical composition of claim 6, which is for therapeutic applications.

9. A marker specific to a human embryonic stem cell, comprising the nucleic acid molecule of claim 1.

10. The marker of claim 9, wherein the human embryonic stem cell is an embryonic carcinoma stem cell.

11. The marker of claim 9, wherein the human embryonic stem cell is an undifferentiated embryonic stem cell.

12. The marker of claim 11, wherein the marker has a nucleotide sequence selected from the group consisting of SEQ ID NO: 1-6.

* * * * *